United States Patent
Fogwill et al.

(10) Patent No.: US 9,625,428 B2
(45) Date of Patent: Apr. 18, 2017

(54) MODULATED FLAME GAS FLOW RATES IN FLAME-BASED DETECTORS

(71) Applicant: Waters Technologies Corporation, Milford, MA (US)

(72) Inventors: Michael O. Fogwill, South Grafton, MA (US); Joseph D. Michienzi, Plainville, MA (US); James P. Murphy, Franklin, MA (US)

(73) Assignee: Waters Technologies Corporation, Milford, MA (US)

( * ) Notice: Subject to any disclaimer, the term of this patent is extended or adjusted under 35 U.S.C. 154(b) by 372 days.

(21) Appl. No.: 14/507,310

(22) Filed: Oct. 6, 2014

(65) Prior Publication Data

US 2015/0101393 A1    Apr. 16, 2015

Related U.S. Application Data

(60) Provisional application No. 61/889,783, filed on Oct. 11, 2013.

(51) Int. Cl.
| | |
|---|---|
| *G01N 7/00* | (2006.01) |
| *G01N 30/38* | (2006.01) |
| *G01F 1/76* | (2006.01) |
| *G01N 1/28* | (2006.01) |
| *G01N 33/00* | (2006.01) |
| *G01N 30/68* | (2006.01) |
| G01N 1/00 | (2006.01) |
| G01N 30/32 | (2006.01) |

(52) U.S. Cl.
CPC .............. *G01N 30/38* (2013.01); *G01F 1/76* (2013.01); *G01N 1/28* (2013.01); *G01N 30/68* (2013.01); *G01N 33/0016* (2013.01); G01N 2001/002 (2013.01); G01N 2030/324 (2013.01)

(58) Field of Classification Search
CPC ....................................................... G01N 7/00
USPC ............................................. 73/23.31, 23.34
See application file for complete search history.

(56) References Cited

U.S. PATENT DOCUMENTS 5,153,673 A * 10/1992 Amirav ................ G01N 27/626
    356/315
5,190,882 A    3/1993 Schulz et al.
(Continued)

FOREIGN PATENT DOCUMENTS

WO          96/06349 A1    2/1996

OTHER PUBLICATIONS

Morrison, F. A., "Compressible Fluids," Michigan Technological University, Nov. 2004, 94-98.
(Continued)

*Primary Examiner* — Michael A Lyons
*Assistant Examiner* — Hoang Nguyen
(74) *Attorney, Agent, or Firm* — McCarter & English, LLP; Deborah M. Vernon

(57) ABSTRACT

Methods and apparatus for the modulation of flame gas stoichiometry to a flame-based detector for use in chromatographic separations are presented. As the total mass flow rate of mobile phase entering the flame-based detector changes (e.g., as a result of density programming in the separation), the mass flow rate of combustion gases to the detector are altered in proportion to the amount of mobile phase entering the detector. As a result, flame stability and sensitivity of the detector can be maintained by the methods and apparatus of the present disclosure.

15 Claims, 22 Drawing Sheets

(56) References Cited

U.S. PATENT DOCUMENTS

| | | | |
|---|---|---|---|
| 5,356,222 A | 10/1994 | Kettner et al. | |
| 5,741,711 A | 4/1998 | Amirav et al. | |
| 7,223,607 B2* | 5/2007 | Bryselbout | G01N 33/0047 422/50 |
| 7,435,080 B2* | 10/2008 | Joklik | F02D 35/0092 431/121 |
| 2001/0030285 A1* | 10/2001 | Miller | G01N 27/624 250/288 |
| 2005/0287033 A1 | 12/2005 | Thurbide | |
| 2008/0213908 A1* | 9/2008 | Thurbide | G01N 21/72 436/73 |
| 2011/0306146 A1 | 12/2011 | Sidhu et al. | |
| 2015/0078962 A1* | 3/2015 | Fogwill | G01N 30/68 422/54 |

OTHER PUBLICATIONS

Klesper, E. et al., "Apparatus and separations in supercritical fluid chromatography," European Polymer Journal, 1978, vol. 14, 77-88.
Tarafder, A. et al., "Use of the isopycnic plots in designing operations of supercritical fluid chromatography: IV. Pressure and density drops along columns," J. Chromatogr. A, 2012, vol. 1238, 132-145.
Shen, J. et al., "Gas-phase selecive oxidation of alcohols: In situ electrolytic nano-silver/zeolite film/copper grid catalyst," Journal of Catalysis, 2006, vol. 237, 94-101.
GB Combined Search and Examination Report, dated Aug. 3, 2015.

* cited by examiner

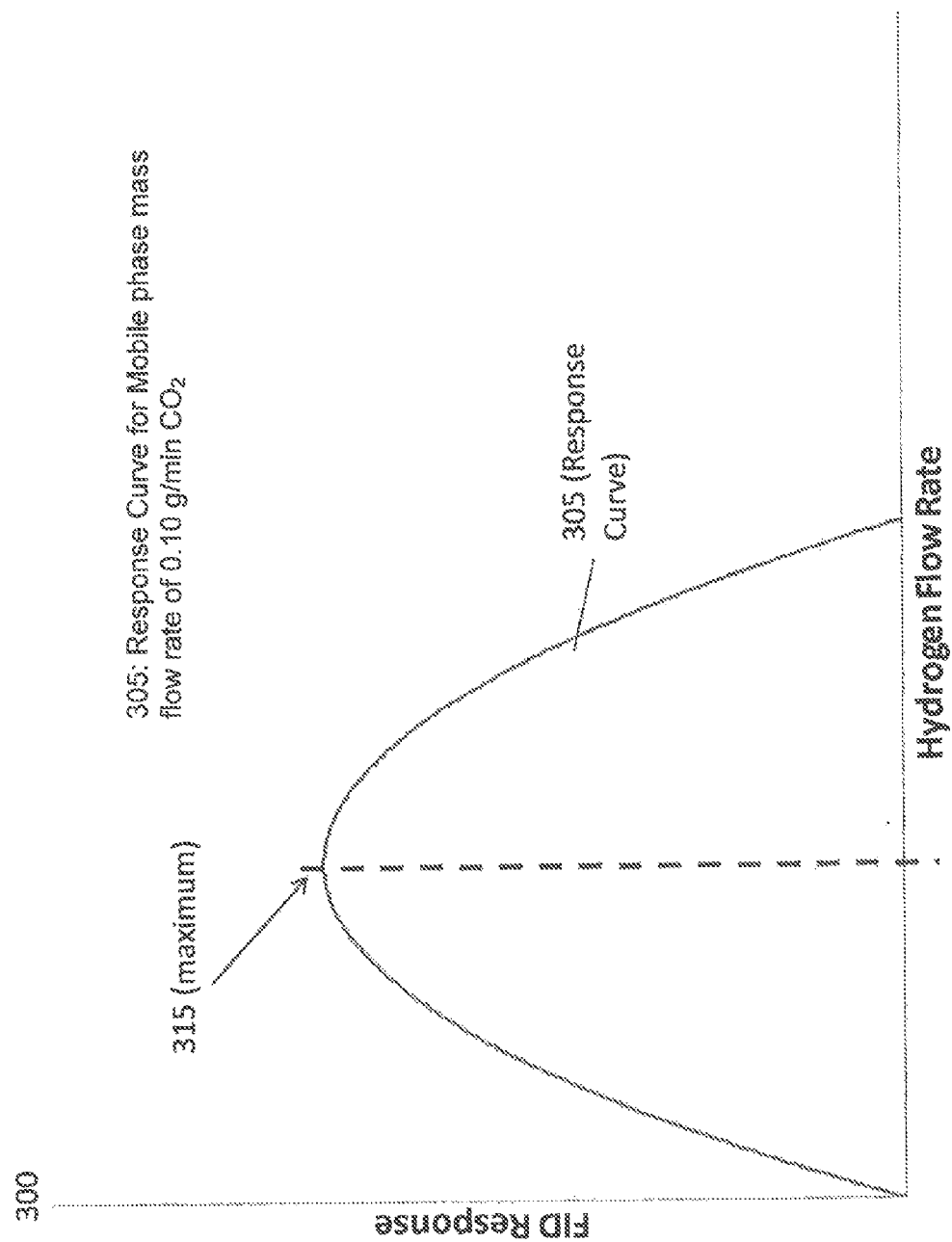

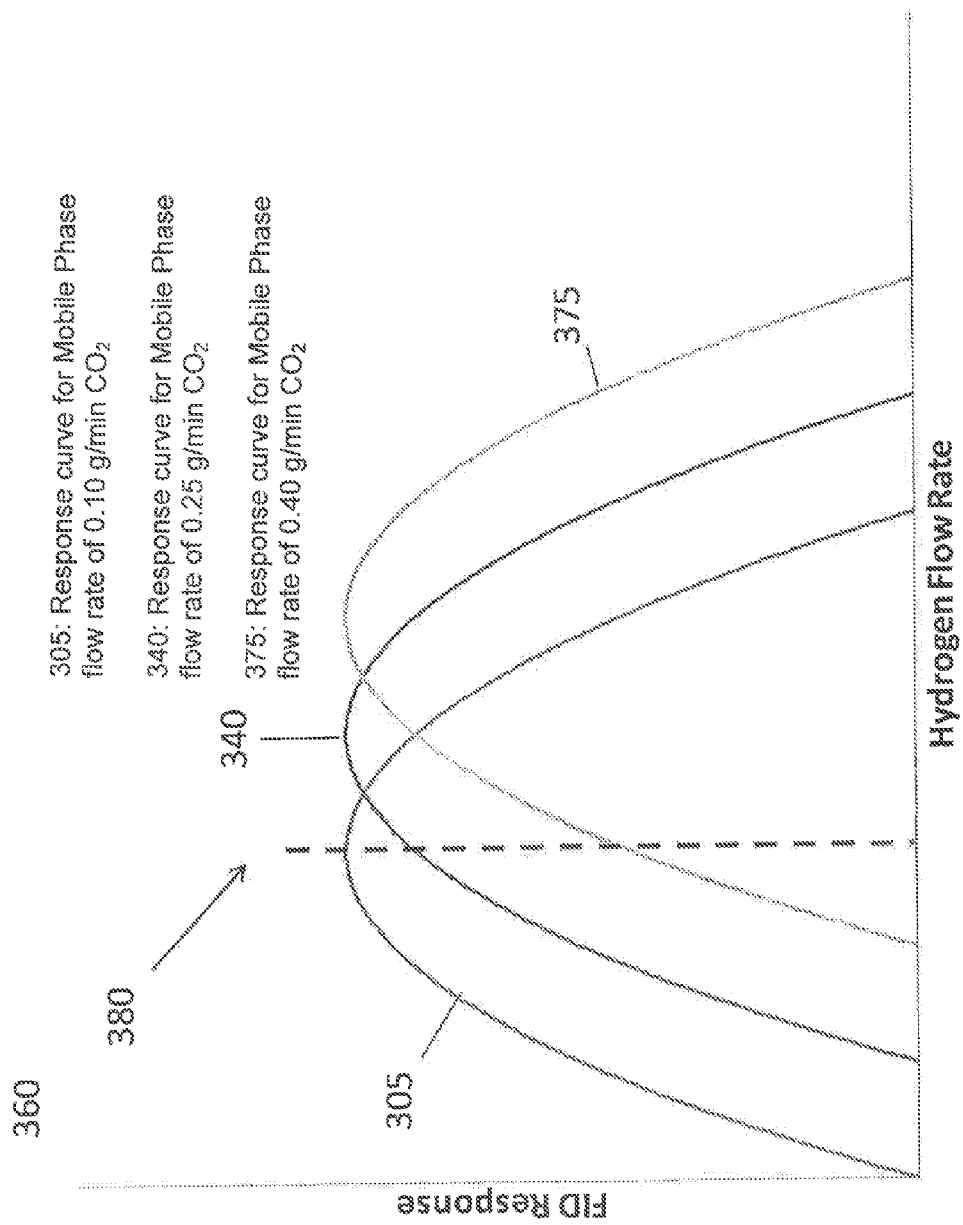

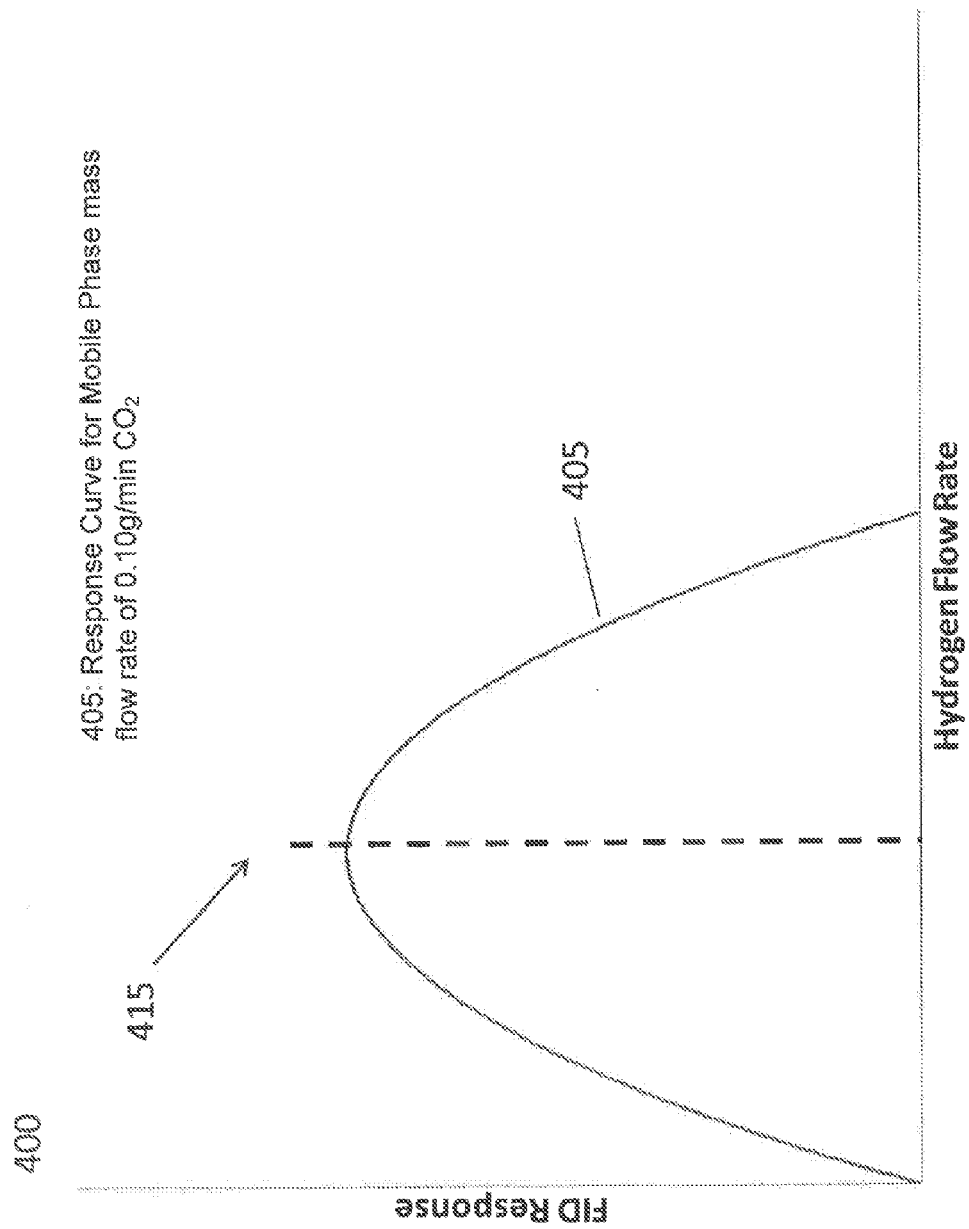

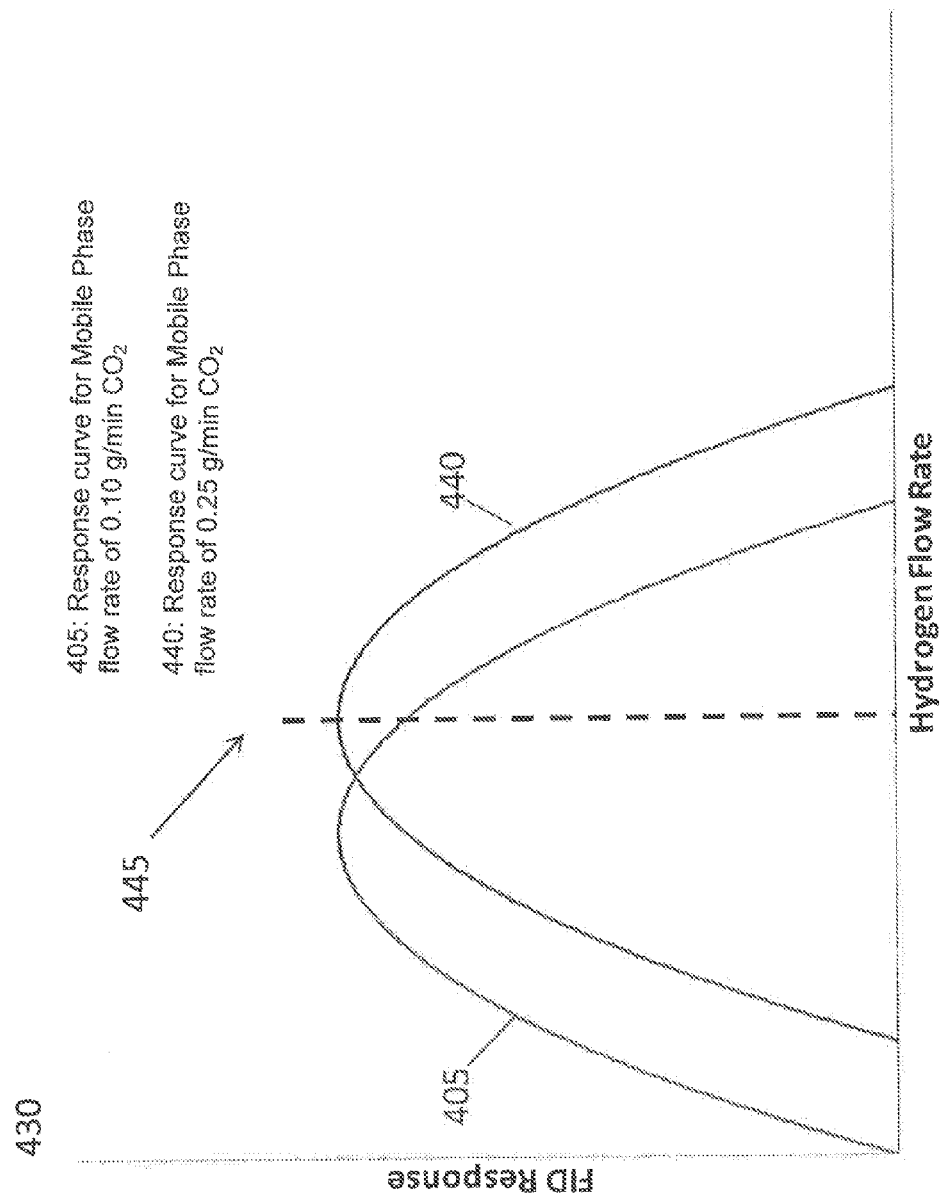

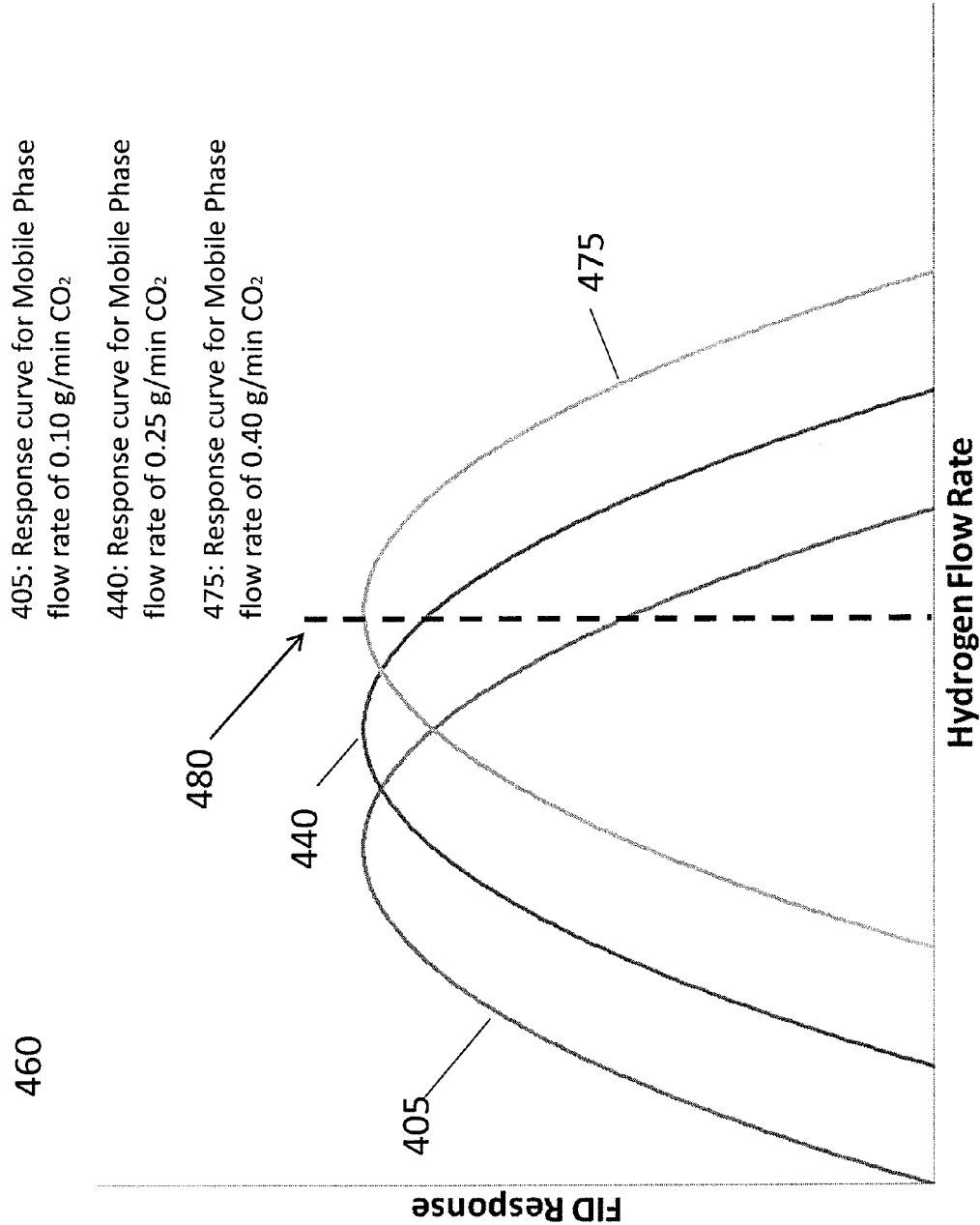

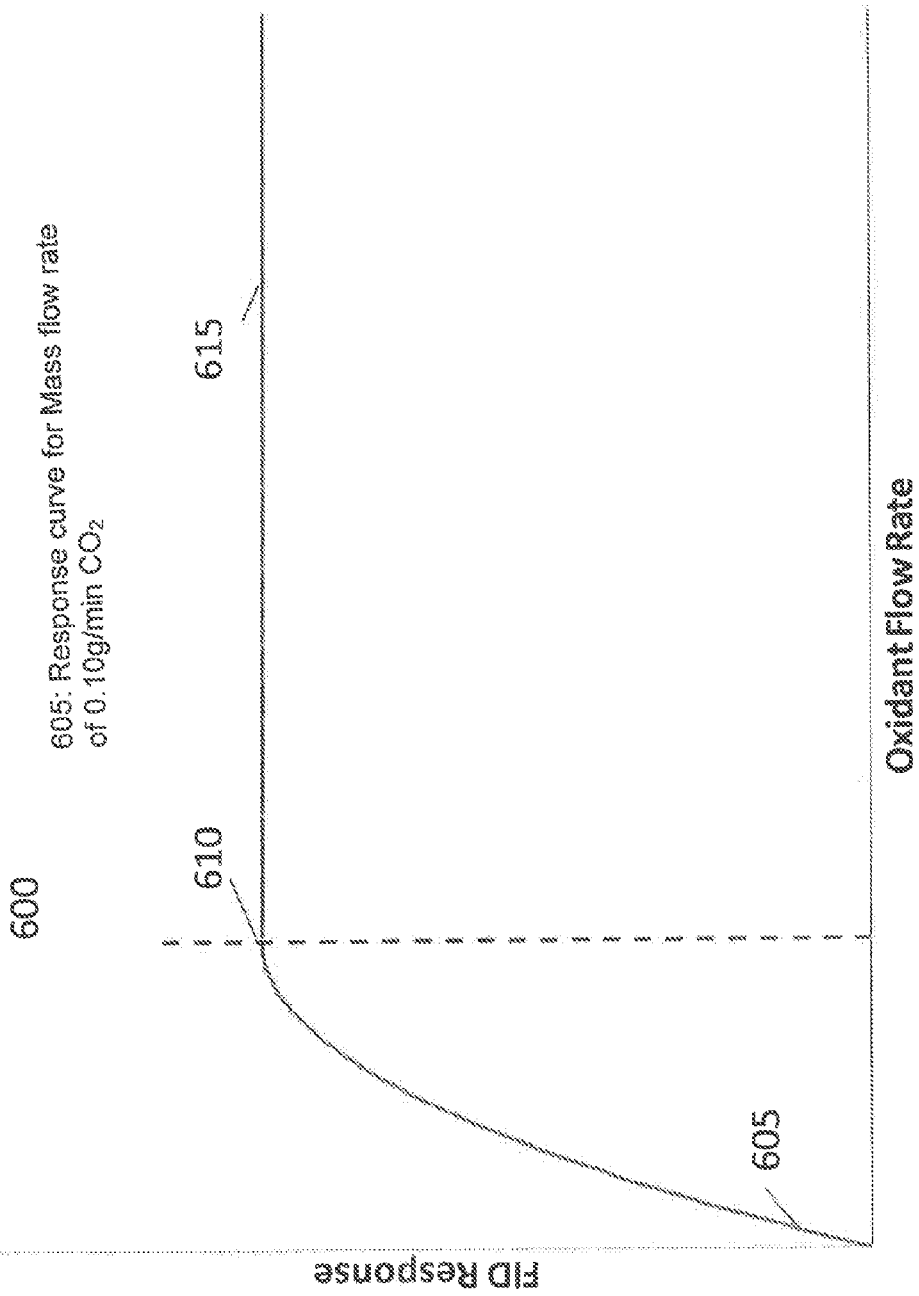

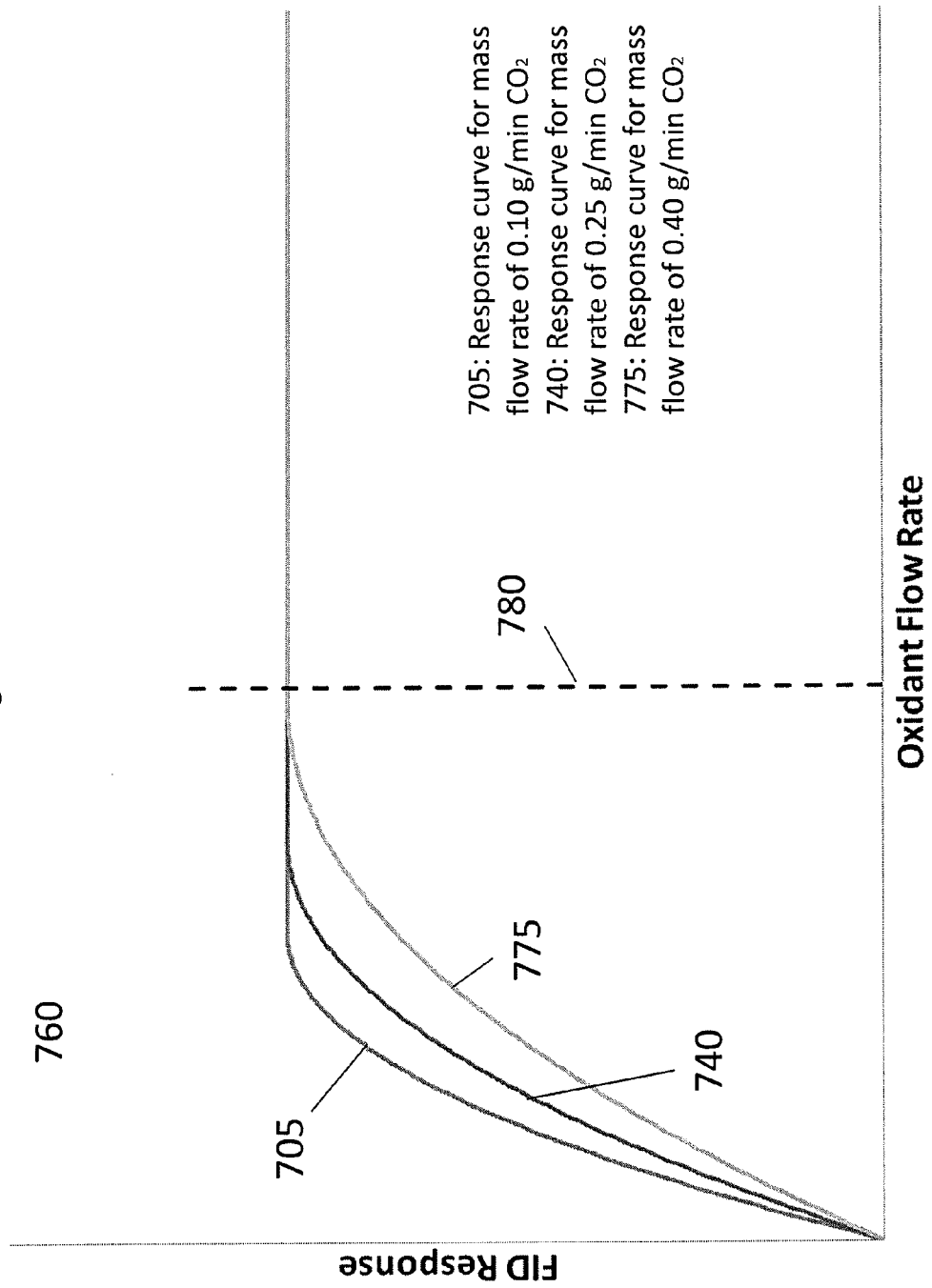

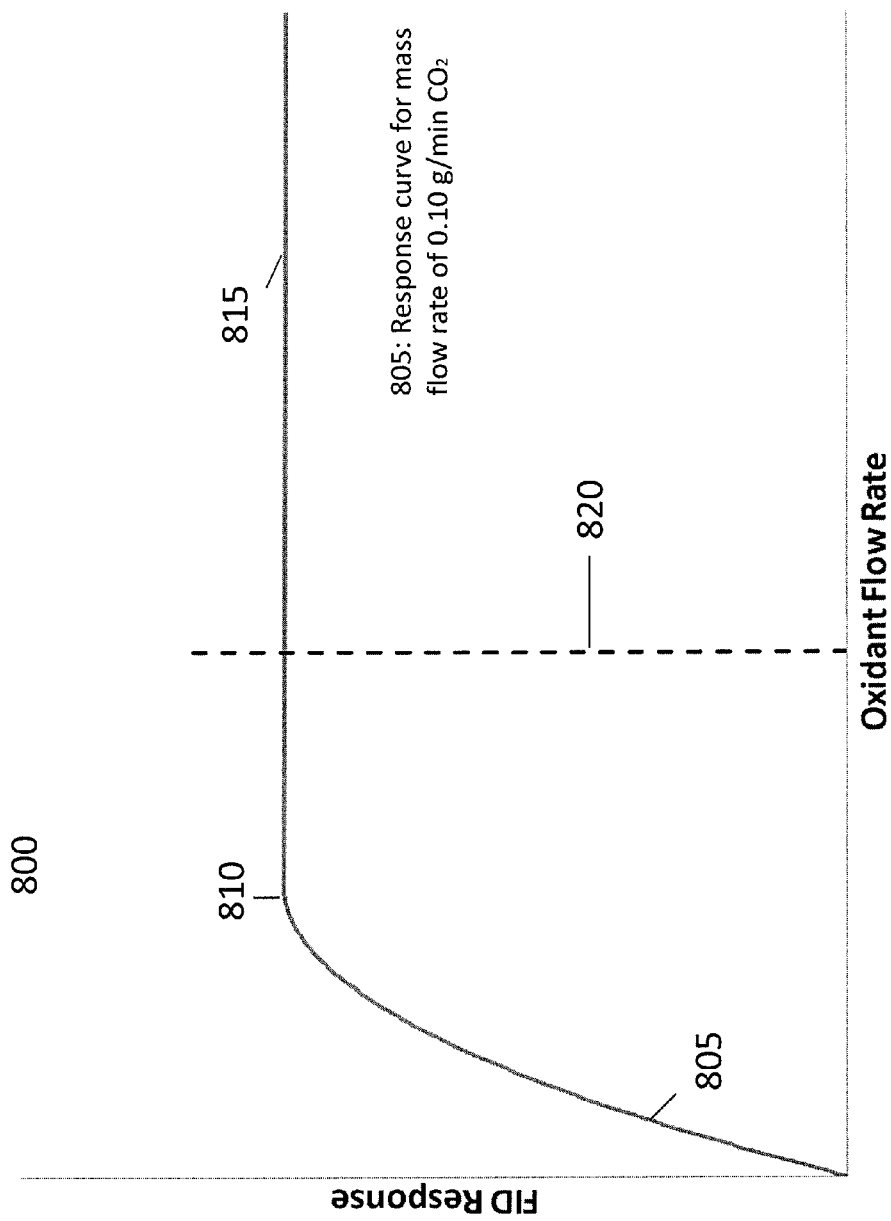

MODULATED FLAME GAS FLOW RATES IN FLAME-BASED DETECTORS

CROSS-REFERENCE TO RELATED APPLICATIONS

This application claims priority to and the benefit of U.S. Provisional Application No. 61/889,783 filed Oct. 11, 2013, and entitled "Modulated Flame Gas Flow Rates In Flame-Based Detectors" which is incorporated herein by reference in its entirety.

TECHNICAL FIELD

The present disclosure is directed to methods and related apparatus for the modulation of flame gas mass flow rates to a flame-based detector. In the context of density-programmed gradient chromatographic separations, for example, the technology provides for methods and related apparatus to adjust (e.g., increase or decrease) the mass flow rate of combustion gases (e.g., hydrogen and/or oxygen) to a flame-based detector in response to changes in the mass flow rate of a mobile phase fluid (e.g., carbon dioxide) entering the detector.

BACKGROUND

Flame-based detection is a common technique used in chromatography (e.g., gas chromatography) to detect analytes of interest (e.g., organic compounds) in an analyte stream. For instance, flame ionization detection (FID) functions by maintaining a flame via the addition of a combustible fuel (e.g., hydrogen) and an oxidant (e.g., oxygen) to the detector. An analyte stream (e.g., the eluent from a gas chromatography column) passes through the flame in the flame ionization detector. Compounds that contain a reduced form of carbon (e.g., organic compounds from the analyte stream) are ionized in the flame to produce carbon-based ions and free electrons. Compounds without reduced carbon such as carbon dioxide, nitrogen and noble gases (e.g., helium) do not. The newly-generated free electrons are attracted to a positive electrode (e.g., anode) while the carbon-based ions are attracted to a negative electrode (e.g., cathode). As the ions and electrons reach their respective electrodes, an electric current is established. The amount of current flow is thus proportional to the number of reduced carbon atoms entering the flame ionization detector. Accordingly, flame ionization detectors are very selective for, and can accurately measure the presence of, analytes of interest that contain carbon (e.g., organic compounds).

Flame photometric detection (FPD) is another technique used in chromatography (e.g., gas chromatography) to detect analytes of interest (e.g., small organic or organometallic compounds) in an analyte stream. FPDs also maintain a flame supplied by a combustion gas (e.g., a combustible fuel and/or an oxidant). Instead of measuring current generated via the ionization of carbon-based compounds, flame photometric detectors measure the light emitted when analytes (e.g., compounds capable of chemiluminescence in a flame) combust. In some cases, certain atoms (e.g., sulfur, phosphorous, tin, chromium or tellurium) can emit light at specific wavelengths upon combustion, thus enabling a practitioner to selectively determine the presence of a given analyte of interest by measuring for excitation at a specific wavelength unique to an atom known to be present in the analyte of interest.

In general, there are a number of different mobile phase fluids used in chromatography. Various chromatographic systems can use different mobile phase fluids depending on the nature of the separation to be carried out. For instance, liquids (e.g., acetonitrile), gases (e.g., helium), or compressible fluids, (e.g., carbon dioxide) can serve as a mobile phase. In addition, when employing a compressible fluid as a mobile phase, the density of the mobile phase can be increased or decreased over the course of a chromatographic separation while the volumetric flow rate is kept constant (e.g., a density-programmed gradient separation).

In chromatographic systems using flame-based detection, the use of density programming can interfere with the detection of analyte molecules. For instance, the mass flow rates of combustible fuels and/or oxidants (e.g., hydrogen and/or oxygen) to a flame-based detector can be optimized according to the mass flow rate of mobile phase fluid (e.g., carbon dioxide) at the beginning of a separation. A change in mass flow rate of mobile phase fluid during the separation resulting from the use of density programming can cause instability in the flame and decreased detector performance. In an extreme example, the flow rates of the combustible fuels and/or oxidants that were optimized for best response at the beginning of a separation can be inadequate to maintain a stable flame at some point later in the separation if a density program is used.

SUMMARY OF THE INVENTION

The present disclosure is directed to methods for maintaining optimum flame characteristics in a flame-based detector of a chromatographic system using a density program or otherwise having variable mobile phase mass flow rates. For example, when the mass flow rate of mobile phase fluid (e.g., carbon dioxide) entering a flame-based detector is increased, it can result in less than optimal detector response to the analyte. In some cases, it can destabilize or even suffocate and extinguish the flame. Accordingly, it can be necessary to provide increased fuel and/or oxidant to the flame-based detector (e.g., hydrogen and/or air) to support the flame in the presence of increased mass flow rates of mobile phase gases, and vice-versa. The present disclosure provides methods for adjusting the mass flow rate of combustion gases (e.g., a combustible fuel such as hydrogen and/or oxidant such as oxygen or air) entering a flame-based detector in response to, and in proportion to, the mass flow rate of mobile phase fluid (e.g., carbon dioxide) entering the detector.

When conducting a chromatographic separation which employs density programming and flame-based detection, the response of the flame-based detector can be optimized for one mass flow rate of the mobile phase. At other mobile phase mass flow rates, however, detector performance can suffer reduced sensitivity. This varying detector response can also reduce confidence in the results when quantifying individual analytes of a chromatographic separation. In general, the present disclosure relates to methods that can maintain optimum detector performance throughout an entire density-programmed chromatographic separation. This normalization of response can help increase confidence in the quantitative results of a chromatographic separation by ensuring that all regions of a chromatogram accurately reflect the mass flow rate of carbon (i.e., analyte) entering a flame-based detector at a given time point. Automated management of flame gas flow rates (e.g., hydrogen and oxygen) can be provided by feedback from system parameters, such as pressure, temperature, or density, or from the mass flow rate of mobile phase fluid directed to the detector in the chromatographic system. Accordingly, the present technology substantially eliminates and/or reduces variability in the flame-based detector response when performing density gradient separations.

In one aspect, the present technology provides a method for maintaining flame characteristics in a flame-based detector. That method can include providing a chromatographic system having a mobile phase flow stream in fluid communication with the flame-based detector and upstream of the detector, wherein the mobile phase flow stream has an adjustable mass flow rate, determining a mass flow rate of a non-combustion portion of a flow stream entering the flame-based detector, and adjusting a mass flow rate of a combustion gas entering the flame-based detector in response to the mass flow rate of the non-combustion portion of the flow stream entering the detector. In preferred embodiments, additional combustion gas is added with respect to the determined mass flow rate of the non-combustion portion of the flow stream.

In another aspect, the technology provides a method for maintaining flame characteristics in a flame-based detector. The method can include providing a chromatographic system in fluid communication with the flame-based detector and upstream of the detector, pre-determining a density gradient and a volumetric flow rate of a non-combustion portion of a flow stream entering the flame-based detector over a given period of time and using the density gradient and volumetric flow rate to determine a mass flow rate of the non-combustion portion of the flow stream at any time point within the period of time, followed by adjusting the mass flow rate of a combustion gas entering the flame-based detector in response to the determined mass flow rate of the non-combustion portion of the flow stream entering the detector to maintain flame characteristics. In preferred embodiments, the combustion gas is adjusted with respect to the mass flow rate of the non-combustion portion of the flow stream.

In yet another aspect, the technology provides a method for maintaining flame characteristics in a flame-based detector. The method can include providing a chromatography system in fluid communication with the flame-based detector and upstream of the detector, flowing combustion gas comprising a pre-determined ratio of fuel to oxygen to the flame-based detector, flowing at least a portion of a non-combustible mobile phase flow stream from the chromatographic system to the flame-based detector, flowing a substantially inert makeup gas to the flame-based detector, and adjusting the mass flow rate of makeup gas with respect to the mass flow rate of a non-combustible portion of the flow stream entering the flame-based detector. In preferred embodiments, the total mass flow rate of combined mobile phase flow stream and makeup gas flow portions of the flow stream entering the detector remains constant.

One or more of the aspects provided above can include one or more of the following features. In some embodiments, the chromatographic system is a supercritical fluid chromatographic or a gas chromatographic system. In some embodiments, the non-combustion portion of the flow stream includes, at least in part, carbon dioxide ($CO_2$), nitrogen ($N_2$), argon (Ar), xenon (Xe), nitrous oxide ($N_2O$), helium (He) or a chlorofluorocarbon (CFC). Also, the mass flow rate of the non-combustion portion of the flow stream entering the flame-based detector at a given time point can be determined based on density and volumetric flow rate of the non-combustion portion of the flow stream at that time point. The density and volumetric flow rate of the non-combustion portion of the flow stream can be monitored substantially continuously (e.g., substantially in real time) by sensors coupled to a computer system. A computer system can automatically adjust the mass flow rate of one or more of the combustion gases entering the flame-based detector at a given time point in response to the determined mass flow rate of the non-combustion portion of the flow stream entering the detector at a given time point. The mass flow rate of combustion gas entering the flame-based detector at a given time point can be pre-determined by a computer according to a pre-determined density program defining density and volumetric flow rate of the non-combustion portion of the flow stream entering the flame-based detector at that time point. The technology can also include adjusting the distance between a burner of the flame-based detector and a collector electrode of the flame-based detector in relation to the size of the flame, or the size of the burner orifice.

In some embodiments, a portion of the non-combustion portion of the flow stream is directed to the flame-based detector by use of a restrictor to separate the flow stream. In one embodiment, the restrictor is a fixed restrictor.

Additionally, the mass flow rate of the non-combustion portion of the flow stream entering the flame-based detector can be monitored in substantially real time by sensors in communication with a computer system. This system can actively adjust the mass flow rate of the combustion gas entering the flame-based detector in response to the actual mass flow rate of the non-combustion portion of the flow stream entering the flame-based detector.

As described herein, the terms "combustion gas," "combustion gases," or "combustible portion of the flowstream" are understood to mean a combustible fuel and/or an oxidant. Thus, in some embodiments, a "combustion gas" includes only a combustible fuel, such as hydrogen gas. In some embodiments, a "combustion gas" includes only an oxidant such as air. In some embodiments, a "combustion gas" includes both a combustible fuel and an oxidant. In some embodiments, the combustible fuel is hydrogen. In some embodiments, the oxidant is oxygen or air.

In one or more embodiments, the flow stream entering the detector can include the combustion gas and a non-combustion portion of the flow stream. The non-combustion portion of the flow stream can include the mobile phase from the chromatographic system. In some embodiments, the mobile phase includes $CO_2$. The non-combustion portion of the flow stream can also include a substantially inert makeup gas. The combustion portion of the flow stream can include the combustion gas.

In another aspect, the technology provides a method for maintaining flame characteristics in a flame-based detector. The method can include providing a chromatographic system having an adjustable flow rate of a mobile phase flow stream in fluid communication with the flame-based detector and upstream of the detector, such that the mobile phase flow stream comprises at least about 80% carbon dioxide. The method can further include determining a mass flow rate of the carbon dioxide portion of the flow stream entering the flame-based detector, and adjusting a mass flow rate of a combustion gas entering the flame-based detector in response to the mass flow rate of the carbon dioxide portion of the flow stream entering the detector to maintain flame characteristics, such that the combustion gas is adjusted with respect to the determined mass flow rate of the carbon dioxide portion of the flow stream.

In one or more embodiments, an indirect mass flow rate of the carbon dioxide portion of the flow stream entering the flame-based detector at a given time point is determined based on density and volumetric flow rate of the carbon dioxide portion of the flow stream at that time point. In one or more embodiments, the density and volumetric flow rate of the carbon dioxide portion of the flow stream are monitored substantially continuously by sensors coupled to a computer system.

In one or more embodiments, the computer system automatically adjusts the mass flow rate of combustion gas entering the flame-based detector at a given time point in response to the mass flow rate of the carbon dioxide portion of the flow stream entering the detector at a given time point.

In one or more embodiments, the mass flow rate of combustion gas entering the flame-based detector at a given time point is pre-determined by a computer according to a pre-determined density program defining density and volumetric flow rate of the carbon dioxide portion of the flow stream entering the flame-based detector at that time point. The present disclosure may further include adjusting the distance between a burner of the flame-based detector and a collector electrode of the flame-based detector in relation to the size of the flame. A portion of the carbon dioxide portion of the flow stream may then be directed to the flame-based detector by use of a fixed restrictor to separate the flow stream. In one or more embodiments of the present disclosure, the combustion gas comprises hydrogen gas and air.

In another aspect, the disclosure provides a method for maintaining flame characteristics in a flame-based detector. The method can include providing a chromatographic system in fluid communication with the flame-based detector and upstream of the detector, such that a mobile phase comprises at least 80% carbon dioxide. The method can further include pre-determining a density gradient and a volumetric flow rate of a carbon dioxide portion of the mobile phase entering the flame-based detector over a given period of time. The density gradient and volumetric flow rate can be used to determine a mass flow rate of the carbon dioxide portion of the flow stream at any time point within the period of time. The mass flow rate of combustion gas entering the flame-based detector can be adjusted in response to the determined mass flow rate of the carbon dioxide portion of the flow stream entering the detector to maintain flame characteristics, such that combustion gas can be adjusted with respect to the mass flow rate of the carbon dioxide portion of the flow stream.

In one or more embodiments, the mass flow rate of the carbon dioxide portion of the flow stream entering the flame-based detector may be monitored in substantially real time by sensors in communication with a computer system to determine an actual mass flow rate of carbon dioxide. In some embodiments, the computer system actively adjusts the mass flow rate of the combustion gas entering the flame-based detector with respect to the actual mass flow rate of the carbon dioxide portion of the flow stream entering the flame-based detector. The technology may also include adjusting the distance between a burner of the flame-based detector and a collector electrode of the flame-based detector in relation to the size of the flame. A portion of the carbon dioxide portion of the flow stream may also be directed to the flame-based detector by use of a fixed restrictor to separate the flow stream.

In another aspect, the technology includes a method for maintaining flame characteristics in a flame-based detector. The method includes providing a chromatographic system in fluid communication with the flame-based detector and upstream of the detector such that a mobile phase of the chromatography system comprises at least 80% carbon dioxide. The technology can further include flowing a combustion gas comprising a pre-determined ratio of fuel to oxygen to the flame-based detector, such that the combustion gas comprises a portion of a flow stream entering the detector. The method can further include flowing a substantially inert makeup gas to the flame-based detector, and adjusting the mass flow rate of inert makeup gas with respect to the mass flow rate of a carbon dioxide portion of the flow stream entering the flame-based detector, such that the total mass flow rate of inert makeup gas and carbon dioxide portion of the flow stream entering the detector remains constant.

In general, in a single fluid system, the flow rate of the non-combustion gas entering the flame-based detector is adjusted by the mass flow rate. However, in a multiple fluid system such as one includes carbon dioxide and nitrogen as non-combustion gases, it may be more accurate to adjust volumetric flow rate rather than mass flow rate. For example, in one embodiment, the flow rate of a flow stream entering the flame-based detector that includes a combination of an inert make up gas (e.g. nitrogen) and carbon dioxide is adjusted by volumetric flow rate. In one particular embodiment, adjustment is made to maintain a constant total volumetric flow rate of the expanded carbon dioxide and make up nitrogen gas entering the flame-based detector.

In some embodiments, the mobile phase fluid comprises carbon dioxide and the makeup gas comprises nitrogen gas, argon, or carbon dioxide. In some embodiments, the mass flow rate of the carbon dioxide portion of the flow stream entering the flame-based detector is monitored substantially continuously by sensors in communication with a computer system to determine an actual mass flow rate, such that the computer system actively adjusts the mass flow rate of the combustion gas entering the flame-based detector in response to the actual mass flow rate of the carbon dioxide portion of the flow stream entering the flame-based detector. The technology can also include adjusting the distance between a burner of the flame-based detector and a collector electrode of the flame-based detector in relation to the size of the flame. In some embodiments, a portion of the carbon dioxide portion of the flow stream is directed to the flame-based detector by use of a fixed restrictor to separate the flow stream.

The present technology provides a number of benefits and advantages over current methods and apparatus. For instance, the present technology may allow a user to employ a density gradient to enhance a chromatographic separation while still maintaining an optimized flame in a flame-based detector, and thus maintain confidence in the accuracy of results. In addition, the present technology may enable the sensitivity of a flame-based detector to be optimized over the course of an entire chromatographic run, instead of a portion of the run. By automatically optimizing the amount of combustion gas entering a flame-based detector, the present technology can save time for a practitioner by obviating the need to re-optimize combustion gas flow rates. Further, the technology may help resolve the issue of changing detector response factors over the course of a chromatographic separation with a changing mobile phase mass flow rate (e.g., in density programmed separations). The technology ensures uniformity of response for each compound eluted under a dynamic mobile phase mass flow rate separation (e.g., density programmed conditions). The above advantages and aspects can be more clearly understood in light of the drawings and detailed description outlined below.

BRIEF DESCRIPTION OF THE DRAWINGS

The drawings are not necessarily to scale, emphasis instead generally being placed upon illustrating the principles of the technology. Accordingly, the drawings should be understood as exemplary, model representations of the technology unless otherwise indicated. For example, an FID is regarded as having a near universal response (i.e., an FID produces the same current per unit of carbon per time entering the flame). The present disclosure relates, in part, to instances and conditions wherein the response is not universal (e.g., wherein the response is optimal at the beginning of the density-programmed separation and is lower than optimal at the end of the separation.

FIG. 3A shows a graphical representation of the response of a flame-based detector optimized for a hydrogen flow rate set at a first mass flow rate.

FIG. 3C shows a graphical representation of the response of a flame-based detector optimized for a hydrogen flow rate set at a first mass flow rate and the effect of a third mass flow rate of hydrogen.

FIG. 4A shows a graphical representation of the response of a flame-based detector optimized for a hydrogen flow rate set at a first mass flow rate.

FIG. 4B shows a graphical representation of the response of a flame-based detector optimized for a hydrogen flow rate set at a second mass flow rate.

FIG. 4C shows a graphical representation of the response of a flame-based detector optimized for a hydrogen flow rate set at a third mass flow rate.

FIG. 6A shows a graphical representation of the response of a flame-based detector optimized for an oxidant mass flow rate for a first mass flow rate of mobile phase.

FIG. 7C shows a graphical representation of the response of a flame-based detector optimized for an oxidant mass flow rate for a third mass flow rate of mobile phase.

FIG. 8A shows a graphical representation of the response of a flame-based detector to an oxidant mass flow rate, wherein the oxidant mass flow rate is set to accommodate a range of mobile phase mass flow rates.

DETAILED DESCRIPTION

Figure 1:
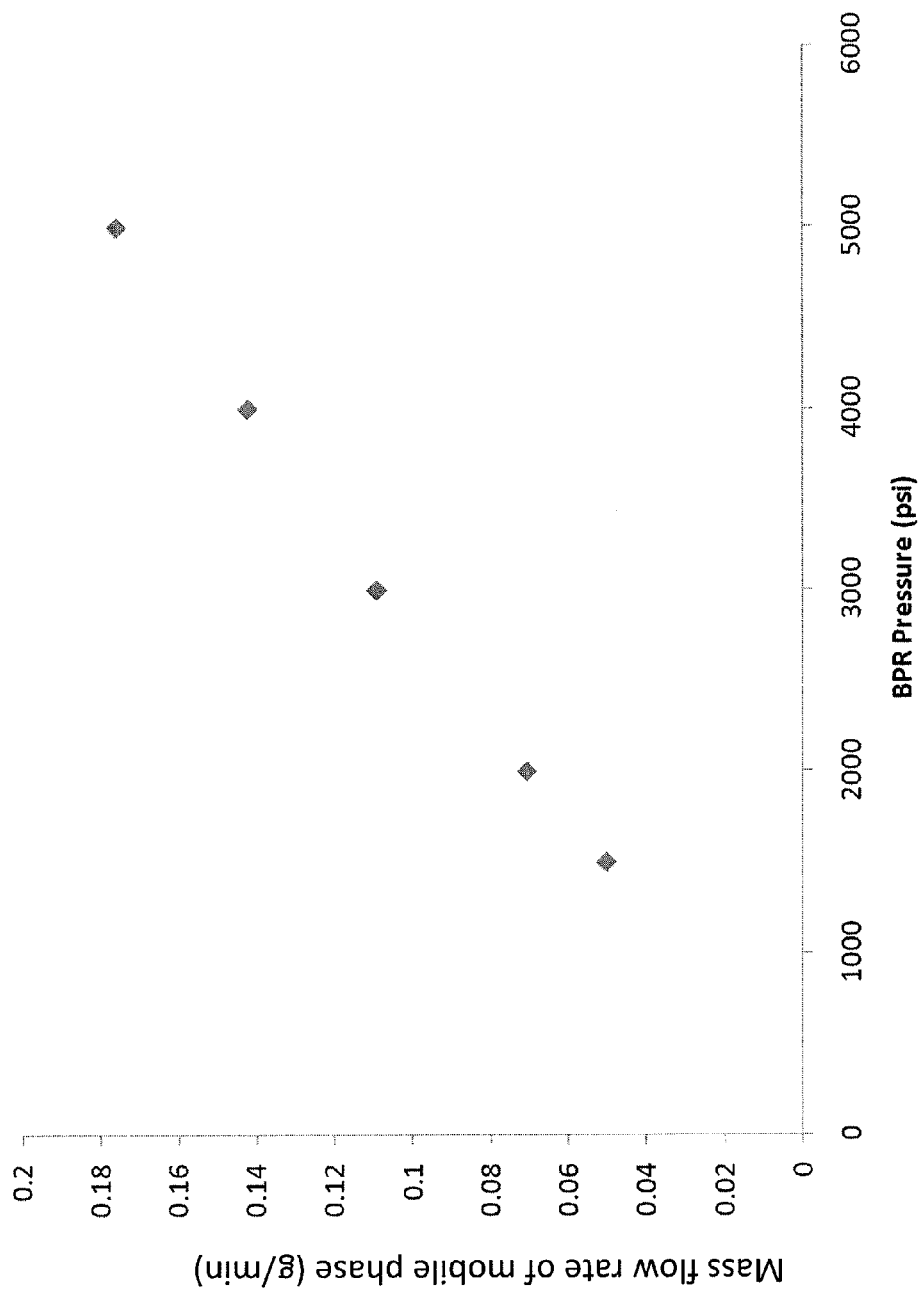
FIG. 1 shows a graph of the mass flow of mobile phase directed to a flame-based detector as a function of the pressure of the mobile phase when employing a split-flow interface.

The present disclosure is directed to methods and related apparatus to modulate the combustion gas flow rate (e.g., hydrogen and/or oxygen) into a flame-based detector to normalize the flame gas stoichiometry while performing a density-programmed gradient chromatographic separation. Density gradients can be used when performing chromatographic separations, including when using a compressible fluid (e.g., carbon dioxide) as a mobile phase. Compressible fluids, compared to liquids such as water, methanol, or acetonitrile, can be difficult to pump and meter as their compressibilities and densities fluctuate during a pump stroke and/or in view of adiabatic heating of the fluid during pumping.

In some applications in which a compressible fluid (e.g., carbon dioxide) is used as a mobile phase, polar modifier fluids (e.g., methanol) can be added to the mobile phase fluid to enhance the separation. However, many polar modifier fluids (e.g., methanol) can interfere with the operation of a flame-based detector. Because many polar modifiers (e.g., methanol) contain reduced forms of carbon, they can induce a response in a flame based detector which produces a signal that does not correspond to the analyte of interest. In some cases, even a very small percentage of a polar modifier such as methanol (e.g., <1% of mobile phase) entering a flame-based detector can be enough to overwhelm the response from the analyte of interest, thus decreasing the utility of the flame-based detector.

A practitioner of ordinary skill will understand that all fluids (e.g., gases and liquids) theoretically have some finite degree of compressibility. That is, all fluids will theoretically respond with a change in volume upon application of a pressure to the fluid. However, in the case of many liquids, (e.g., water, methanol, acetonitrile, isopropyl alcohol) the degree of compressibility is negligible and can be ignored for the purposes of a chromatographic separation.

The term "compressible fluid" as used herein is understood to mean a fluid that is substantially compressible and that is suitable for use as a mobile phase in a chromatographic system. For example, a compressible fluid may be one for which compressibility is actively monitored and/or compensated for throughout each pump stroke and throughout the entire chromatographic apparatus. A compressible fluid for use in chromatography is also one that is attainable for chromatographic systems. For instance, water can be considered a compressible fluid when it exists in a supercritical state. However, in water, the critical point occurs at about 647 K (374° C.; 705° F.) and 22.064 MPa (3200 PSIA or 218 atm). These conditions can often be difficult to achieve using commonly available laboratory (e.g., chromatography) equipment. Alternatively, carbon dioxide exists as a supercritical fluid above its critical temperature (304.25 K) and critical pressure (72.9 atm/7.39 MPa). These conditions can be much more readily achievable in a typical laboratory setup. Some exemplary compressible fluids for use in chromatography are carbon dioxide ($CO_2$), nitrous oxide ($N_2O$), chlorofluorocarbons (CFCs), nitrogen gas ($N_2$), xenon gas (Xe) and argon gas (Ar).

In order to facilitate the use of a flame-based detector (e.g., a flame ionization detector or a flame photometric detector) in a chromatographic separation using a compressible fluid (e.g., carbon dioxide) as the mobile phase, density gradients can be used in place of composition gradients to increase peak capacity. As used herein, the term "density gradient" is used to explain a technique or process by which a mobile phase comprising a compressible fluid is pumped at varying pressures throughout the course of a chromatographic separation. The change in pressure applied to the compressible fluid in turn changes the density of the compressible fluid. In some preferred embodiments, the pressure is increased over the course of a separation, leading to a mobile phase that exists at a higher density at the end of the separation than at the beginning of the separation. In some embodiments, the increase in density of the mobile phase means that a greater mass of the mobile phase is flowed through the chromatographic system per unit of time (e.g., if the volumetric flow rate is held constant).

The increased density of the mobile phase fluid (e.g., carbon dioxide) can help speed the elution of late-eluting analytes of interest from a column while preserving the resolution of early eluters. However, the use of a density gradient causes a change in the total mass flow rate of mobile phase fluid (e.g., carbon dioxide) to a flame-based detector. Although a pump can be programmed to maintain a constant flow rate of mobile phase fluid traveling through a chromatographic column, an increase (or decrease) in system pressure (i.e., density) causes a respective increase (or decrease) in mass flow of mobile phase fluid (e.g., carbon dioxide) directed to the detector.

FIG. 1 is a graph showing the mass flow of mobile phase directed to a flame-based detector as a function of pressure of the mobile phase when employing a split flow interface. The volumetric flow rate of the mobile phase along the column is constant. Although the volumetric flow rate is kept constant by the pump, the mass flow rate directed along the split leg to the detector increase proportionately with system pressure since the split restrictor provides a constant resistance to flow. As the density and pressure of the mobile phase change (e.g., as mobile phase density increases over the course of a density-programmed separation), the total mass of mobile phase entering a detector can change as well.

Figure 2:
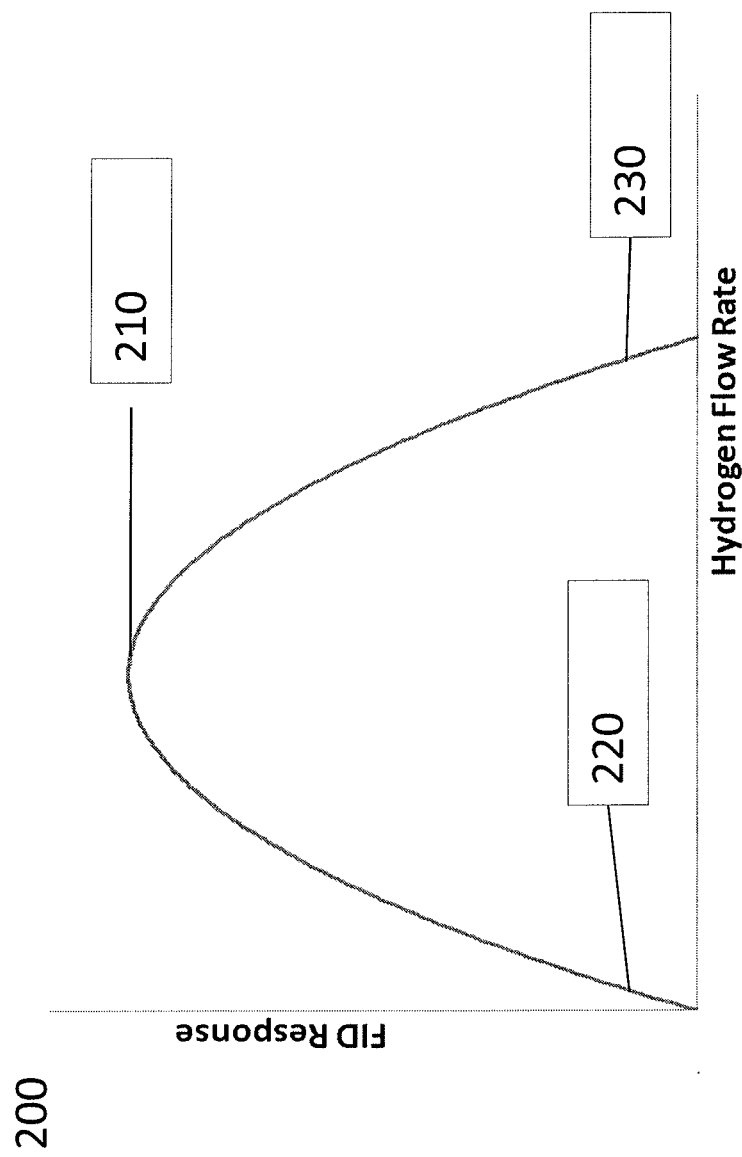
FIG. 2 shows a graphical representation of the response of a flame-based detector to the mass flow rate of hydrogen.

FIG. 2 shows a graph illustrating the theoretical optimization curve of a flame-based detector with detector response (on the y axis) as a function of combustible fuel (e.g., hydrogen) mass flow rate to the detector (on the x axis). As seen in the graph (200), the response of a flame-based detector reaches a maximum (210) at an intermediate mass flow rate of combustible fuel (e.g., hydrogen). The response of the flame-based detector is considerably lower at both relatively lower combustible fuel (e.g., hydrogen) flow rates (220) and at relatively higher combustible fuel (e.g., hydrogen) flow rates (230). A flame-based detector can be optimized for a particular combustible fuel mass flow to the detector. When the mobile phase mass flow changes, the flame characteristics of a flame-based detector may no longer be maintained. The response of the detector may no longer be optimized. The present disclosure is directed to maintaining the flame characteristics or response characteristics in a flame-based detector. Preferably, the flame characteristics remain at or near optimal characteristics, which may be determined differently by each separation.

The flame-characteristics may be measured by the physical features of the flame (e.g. size, shape, color, heat intensity) at an initial set of conditions. The present disclosure maintains at least one physical feature of the flame in a flame-based detector within about 50%, or about 40%, or about 30%, or about 20%, or about 10%, or about 5% of the value of physical feature at the initial set of conditions. The present disclosure maintains at least two physical features of the flame in a flame-based detector, wherein the first feature is within about 50%, or about 40%, or about 30%, or about 20%, or about 10%, or about 5% of the value of physical feature at the initial set of conditions, and the second feature is within about 50%, or about 40%, or about 30%, or about 20%, or about 10%, or about 5% of the value of physical feature at the initial set of conditions. In some embodiments, the physical feature is the temperature of the flame or the amount of un-burnt hydrogen or oxidant in the flame exhaust. In other embodiments, the detector response may be empirically evaluated at the beginning, during and at the end of a gradient separation. Therein, the combustion gas (e.g., hydrogen) flow rates during the separation can be estimated or calculated and pre-set or pre-programmed such that the detector response remains at or near optimal characteristics. Pressure feedback at the back pressure regulator, for example, may be used to control the hydrogen addition rate in a split-flow or post-column addition configuration.

The flame-based characteristics may also be measured by the FID Response remaining at or near the maximum value as determined at the beginning of the separation. The present disclosure maintains the FID Response within about 50%, or about 40%, or about 30%, or about 20%, or about 10%, or about 5% of the maximum value determined at the beginning of the separation. The flame-based characteristics may also be measured by reducing changes to detector response factors over the course of a chromatographic separation. The present disclosure maintains detector response factors over the course of a chromatographic separation within about 50%, or about 40%, or about 30%, or about 20%, or about 10%, or about 5% of their original value determined at the beginning of the separation. In one embodiment, the mass of the injected analyte is known and multiple injections of the analyte may be made during the separation while monitoring the FID response. Periodic injections of an un-retained compound, for example, maybe made. Therein, adjustments (e.g. flow rates, burner to collector distance) can be made during the separation or used to pre-set or pre-program successive separations.

The response of a flame-based detector depends on the mass flow rate of combustion gas (e.g., hydrogen) to the detector. If the mass flow rate of combustion gas (e.g., hydrogen and oxygen) to the detector is low or very low relative to the total mass flow rate, there may not be enough hydrogen entering the detector to support a flame. Accordingly, the stability of the flame will be compromised (e.g., the flame can be too large or too small). In an extreme case, the flame can go out. Alternatively, if the mass flow rate of combustion gas (e.g., hydrogen) to the detector is high or very high (e.g., much greater than the detector is designed to accommodate), the flame may be unstable, or become problematic. For instance, when using a flame ionization detector, supplying too much hydrogen to the detector could cause a flame to grow so large that it spans the collector-polarizer gap. This can short circuit the detector resulting in the detector giving a constant maximum signal.

In addition to decreasing flame stability, an inadequate or overly large supply of combustible fuel (e.g., hydrogen) to the detector can interfere with the sensitivity of the detector in other ways. For instance, if not enough combustible fuel (e.g., hydrogen) reaches a flame-based detector (e.g., FID), there may be not enough combustible fuel to efficiently ionize the reduced carbon in an analyte sample (i.e. reduced detector sensitivity). Therefore, in preferred embodiments sufficient combustible fuel (e.g., hydrogen) reaches a flame-based detector to ensure that the detector maintains optimum sensitivity toward the analyte. In one embodiment, the conditions within a flame-based detector are such that there is maximum ionization efficiency of an analyte (e.g., most signal generated or substantially the most signal generated per unit mass of injected analyte).

FIG. 3A shows a graph (300) illustrating the theoretical response of a flame-based detector as a function of hydrogen mass flow rate when the mobile phase is set to a first mass flow rate entering the detector, for instance about 0.10 g/min carbon dioxide. Note, the mass flow rates provided in the Figures (e.g., 0.10, 0.25 and 0.40 g/min) are illustrative only. The response curve (305) shows a maximum or optimized flame-based detector response (315) at the first mobile phase mass flow rate.

Figure 3B:
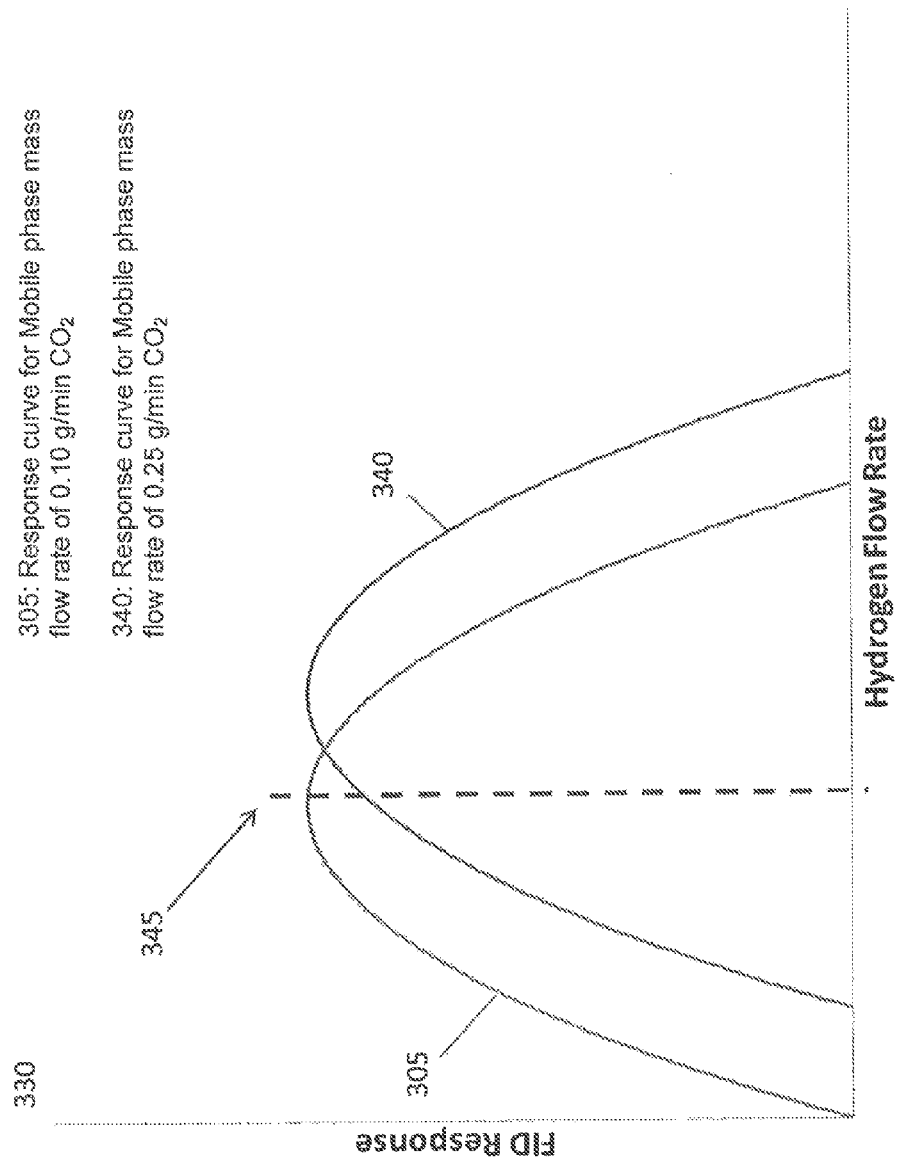
FIG. 3B shows a graphical representation of the response of a flame-based detector optimized for a hydrogen flow rate set at a first mass flow rate and the effect of a second mass flow rate of hydrogen.

FIG. 3B shows an illustrative graph (330) illustrating the theoretical optimized response of a flame-based detector as a function of hydrogen mass flow rate when the mobile phase is set to a first mass flow rate entering the detector, for instance about 0.10 g/min carbon dioxide (305) and when the mobile phase is set to a second mass flow rate entering the detector, for instance about 0.25 g/min carbon dioxide (340). When the flame-based detector response is optimized for the first mobile phase mass flow rate, the detector response when the mobile phase mass flow rate is at the second mass flow rate is suboptimal (see dashed line 345). The change in mobile phase mass flow rate from a first to a second mass flow rate, (e.g., from 0.10 to 0.25 g/min carbon dioxide) can occur over the course of a chromatographic separation as a result of a density gradient. A change in mass flow rate of mobile phase (e.g., carbon dioxide) without re-optimizing the detector response can result in suboptimal performance of a flame-based detector.

FIG. 3C shows a graph (360) illustrating the theoretical optimized response of a flame-based detector response as a function of hydrogen mass flow rate when the mobile phase is set to a first flow rate entering the detector, for instance about 0.10 g/min carbon dioxide (305), when the mobile phase is set to a second mass flow rate entering the detector, for instance about 0.25 g/min carbon dioxide (340), and when the mobile phase is set to a third mass flow rate entering the detector, for instance about 0.40 g/min carbon dioxide (375). Similar to FIG. 3B, when the flame-based detector response is optimized for a first mobile phase mass flow rate (e.g., about 0.10 g/min), the detector response when the mobile phase entering the detector is set to the second or the third mass flow rate (e.g., about 0.25 g/min or 0.40 g/min) is suboptimal (see dashed line 380). The impact on the response of the flame-based detector can become greater the more a mobile phase mass flow rate deviates from the mobile phase mass flow rate used to optimize the detector. The change in mobile phase mass flow rate from a first to a second to a third (e.g., from about 0.1 g/min to about 0.25 g/min and/or about 0.40 g/min) can occur over the course of a chromatographic separation as a result of a density gradient. Therefore a change in mass flow rate of mobile phase (e.g., carbon dioxide) without re-optimizing the detector response, can result in suboptimal performance of a flame-based detector.

Separations that use carbon dioxide or other compressible fluids as a component of the mobile phase can suffer from reduced sensitivity of a flame-based detector because of the lack of control of combustion gases entering the flame-based detector. The present technology provides methods and apparatus to adjust the mass flow rate of combustion gases entering a flame-based detector in response to changes in the mass flow rate of mobile phase fluid entering the flame-based detector. The present technology provides automated management of flame gases driven by feedback from sensors adapted to measure the mobile phase flow properties of the chromatographic system.

FIG. 4A is a graph (400) illustrating the theoretical optimized response of a flame-based detector as a function of hydrogen mass flow rate when the mobile phase is set to a first mass flow rate entering the detector, for instance about 0.10 g/min carbon dioxide. The response curve (405) shows a maximum flame-based detector response (415) at the first mobile phase mass flow rate.

FIG. 4B shows a graph (430) illustrating the theoretical optimized response of a flame-based detector as a function of hydrogen mass flow rate when the mobile phase is set to a first mass flow rate entering the detector, for instance about 0.10 g/min carbon dioxide (405) and when the mobile phase is set to a second mass flow rate entering the detector, for instance about 0.25 g/min carbon dioxide (440). As shown, the hydrogen mass flow rate can be increased to optimize the flame-based detector response when the mobile phase entering the detector is set to the second mass flow rate, for instance about 0.25 g/min (445). Thus, the flame-based detector response when the mobile phase is set at a second mass flow rate entering the detector (e.g., 0.25 g/min) can maintain sufficient, or optimal, sensitivity versus a detector response set to accommodate a first mobile phase mass flow rate of e.g., 0.10 g/min. The change in mobile phase mass flow rate from a first to a second mass flow rate (e.g., 0.1 g/min to 0.25 g/min) can occur over the course of a chromatographic separation as a result of a density gradient. Accordingly, optimizing the mass flow rate of hydrogen gas to the flame-based detector over the course of a separation can result in enhanced performance of a flame-based detector and ensure uniformity of response over the course of a density-programmed gradient separation.

FIG. 4C shows a graph (460) illustrating the theoretical optimized response of a flame-based detector as a function of hydrogen mass flow rate when the mobile phase is set to a first mass flow rate entering the detector, for instance about 0.10 g/min carbon dioxide (405), when the mobile phase is set to a second mass flow rate entering the detector, for instance about 0.25 g/min carbon dioxide (440), and when the mobile phase is set to a third mass flow rate entering the detector, for instance about 0.40 g/min carbon dioxide (475). As shown, the hydrogen mass flow rate can be increased to optimize the flame-based detector response when the mobile phase entering the detector is set at a third mass flow rate of for instance 0.40 g/min (480). Thus, the flame-based detector response when the mobile phase entering the detector is set to a third mass flow rate (e.g. 0.40 g/min) can maintain sufficient, or optimal, sensitivity versus a detector response set to accommodate a first or second mobile phase mass flow rate of, for instance, 0.10 g/min or 0.25 g/min respectively. The change in mobile phase mass flow rate from a first to a second to a third (e.g. from 0.10 g/min to 0.25 g/min to 0.40 g/min) can occur over the course of a chromatographic separation as a result of a density gradient. Accordingly, optimizing the mass flow rate of hydrogen gas to the flame-based detector over the course of a separation can result in enhanced performance of a flame-based detector and ensure uniformity of response over the course of a density-programmed gradient separation.

As shown in FIGS. 4A-4C, the present technology provides for active management of combustion gases entering a flame-based detector in response to changes in the mass flow rate of mobile phase fluid entering the detector. For instance, a processor or computer can operate mass flow controllers or electronic pressure controllers which, in turn, regulate the flow rates of combustion gases to the flame-based detector. The processor or computer can receive information from a system pressure transducer and a mobile phase flow rate sensor. Changes in the system pressure can require changes in the combustion gas (e.g., hydrogen) mass flow rate to ensure optimum detector response. Alternatively, changes in the mobile phase flow rate can require changes in the combustion gas (e.g., hydrogen) mass flow rate to ensure optimum detector response. In certain embodiments, the technology provides for determining the optimal detector gas flow rates over a complete or substantially complete range of mobile phase flow rates and system pressures so that the system can alter the combustion gas mass flow rates to ensure optimum detector response over all or substantially all possible mobile phase mass flow rates.

As used herein, the terms "processor" or "computer" refer to hardware or hardware in combination with one or more program(s), such as can be implemented in software. A processor or computer includes devices that processes information and/or executes instructions, such as a simple microcontroller.

The mass flow rate of oxidant (e.g., air) to the detector can be optimized in a similar manner as the mass flow rate of combustible fuel described above. In some embodiments, adjusting the mass flow of oxidant (e.g., air) to the detector can elicit a different response profile in the flame-based detector than adjusting the mass flow rate of combustible fuel. For instance, the detector response can plateau above a certain mass flow rate of oxidizer to the detector. The detector response can be low at lower flow rates of oxidizer to the detector, and can increase to a maximum response as the mass flow rate of oxidizer is increased. The detector can also experience a decrease in response due to increased flame flicker or unmanaged gas (e.g., air) currents within the burner housing at high oxidant flow rates. In some embodiments, however, the detector does not experience a decrease in performance as the mass flow rate of oxidizer continues to increase.

Figure 5:
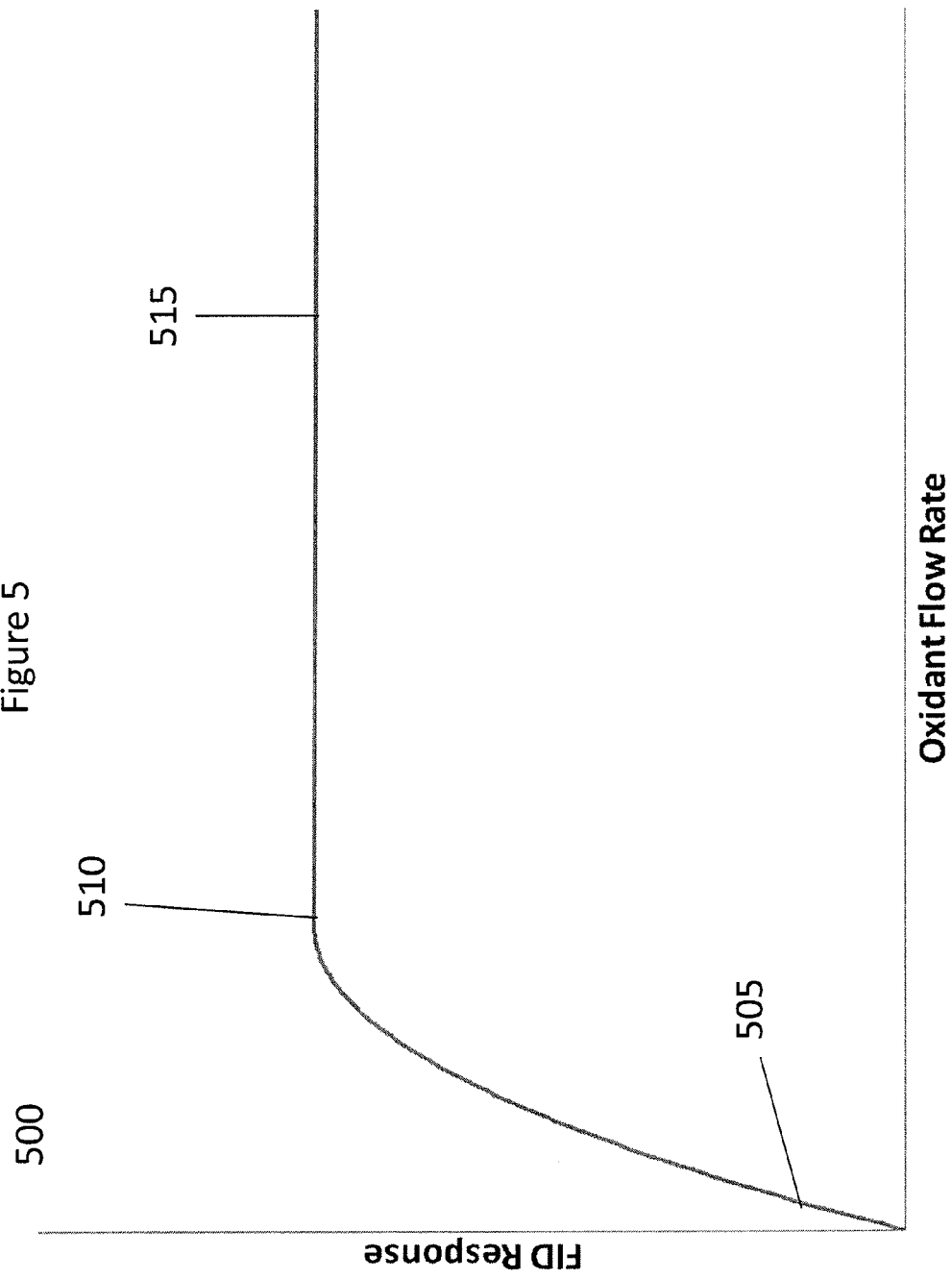
FIG. 5 shows a graphical representation of the response of a flame-based detector to the mass flow rate of oxidant.

FIG. 5 shows a graph illustrating the theoretical optimization curve of a flame-based detector with detector response (on the y axis) as a function of oxidant (e.g., air) flow rate to the detector (on the x axis). As seen in the graph (500), the response of a flame-based detector reaches a maximum at an intermediate mass flow rate (510) of oxidant (e.g., air). The response of a flame-based detector is considerably lower at lower mass flow rates of oxidant to the detector (505). In some preferred embodiments, the response of the detector to oxidant flow rate plateaus at the maximum value and remains largely unchanged from the maximum response as the mass flow rate of oxidant (e.g., air) increases to higher oxidant flow rates (515).

FIG. 6A shows a graph (600) illustrating the theoretical response of a flame-based detector as a function of oxidant (e.g., air) mass flow rate when the oxidant mass flow rate is set to accommodate a mobile phase (e.g., $CO_2$) mass flow rate of about 0.10 g/min. The response curve (605) shows a maximum flame-based detector response (610) at an intermediate oxidant mass flow rate. The maximum detector response plateaus at higher mass flow rates of oxidant flow (615).

Figure 6B:
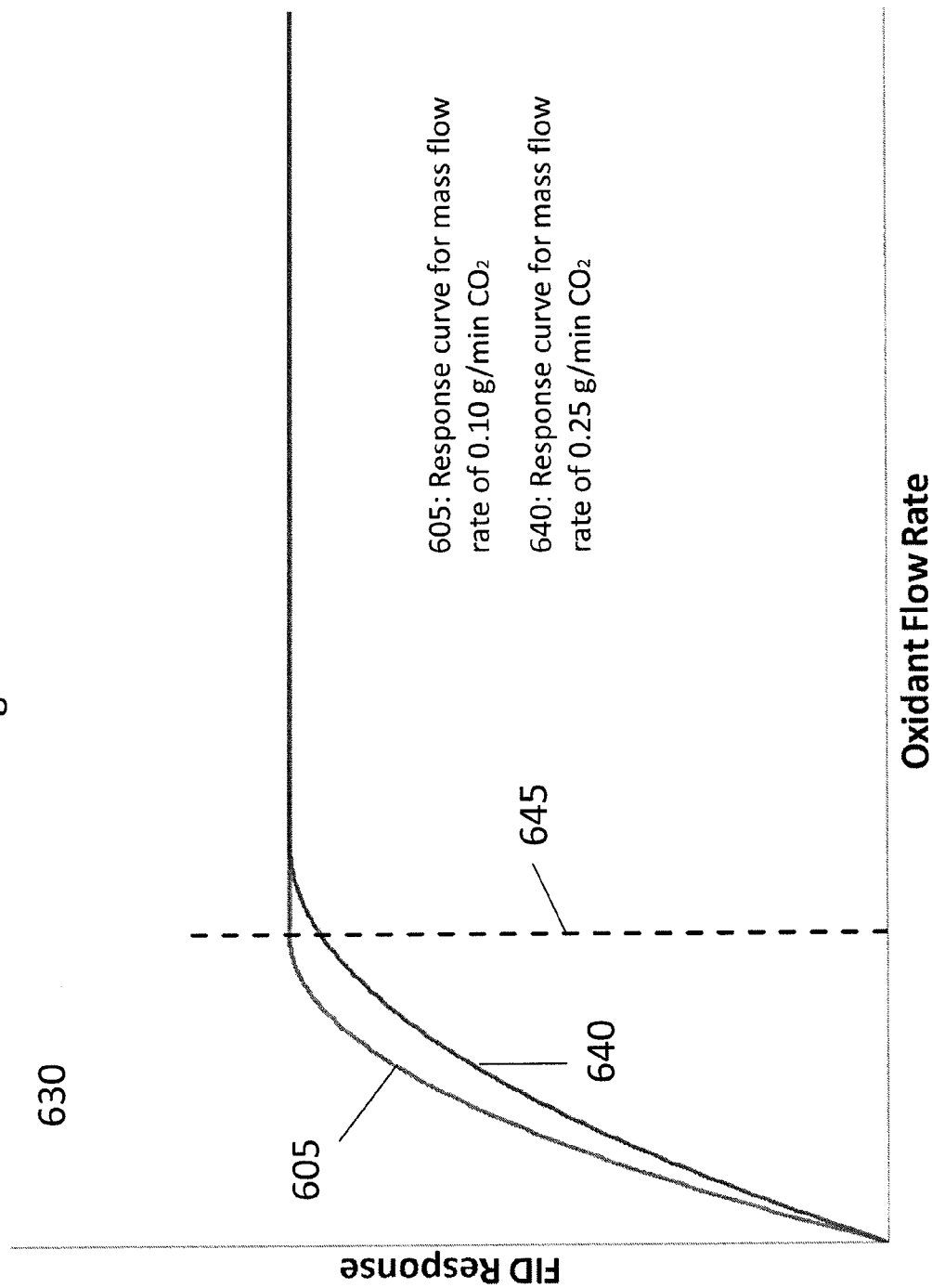
FIG. 6B shows a graphical representation of the response of a flame-based detector optimized for an oxidant mass flow rate for a first mass flow rate of mobile phase and the effect of a second mass flow rate of mobile phase.

FIG. 6B shows a graph (630) illustrating the theoretical response of a flame-based detector as a function of oxidant (e.g., air) mass flow rate when the oxidant mass flow rate is set to accommodate a mobile phase (e.g., $CO_2$) mass flow rate of about 0.10 g/min (605) and about 0.25 g/min (640). When the oxidant mass flow rate is set to optimally accommodate a first mass flow rate of mobile phase (e.g., 0.10 g/min), the detector response when the mobile phase mass flow rate is at the second mass flow rate can be suboptimal (see dashed line 645). The change in mobile phase mass flow rate from a first to a second mass flow rate (e.g. from 0.10 to 0.25 g/min carbon dioxide) can occur over the course of a chromatographic separation as a result of a density gradient. A change in mass flow rate of mobile phase (e.g., carbon dioxide) without re-optimizing the oxidant flow rate can result in suboptimal performance of a flame-based detector.

Figure 6C:
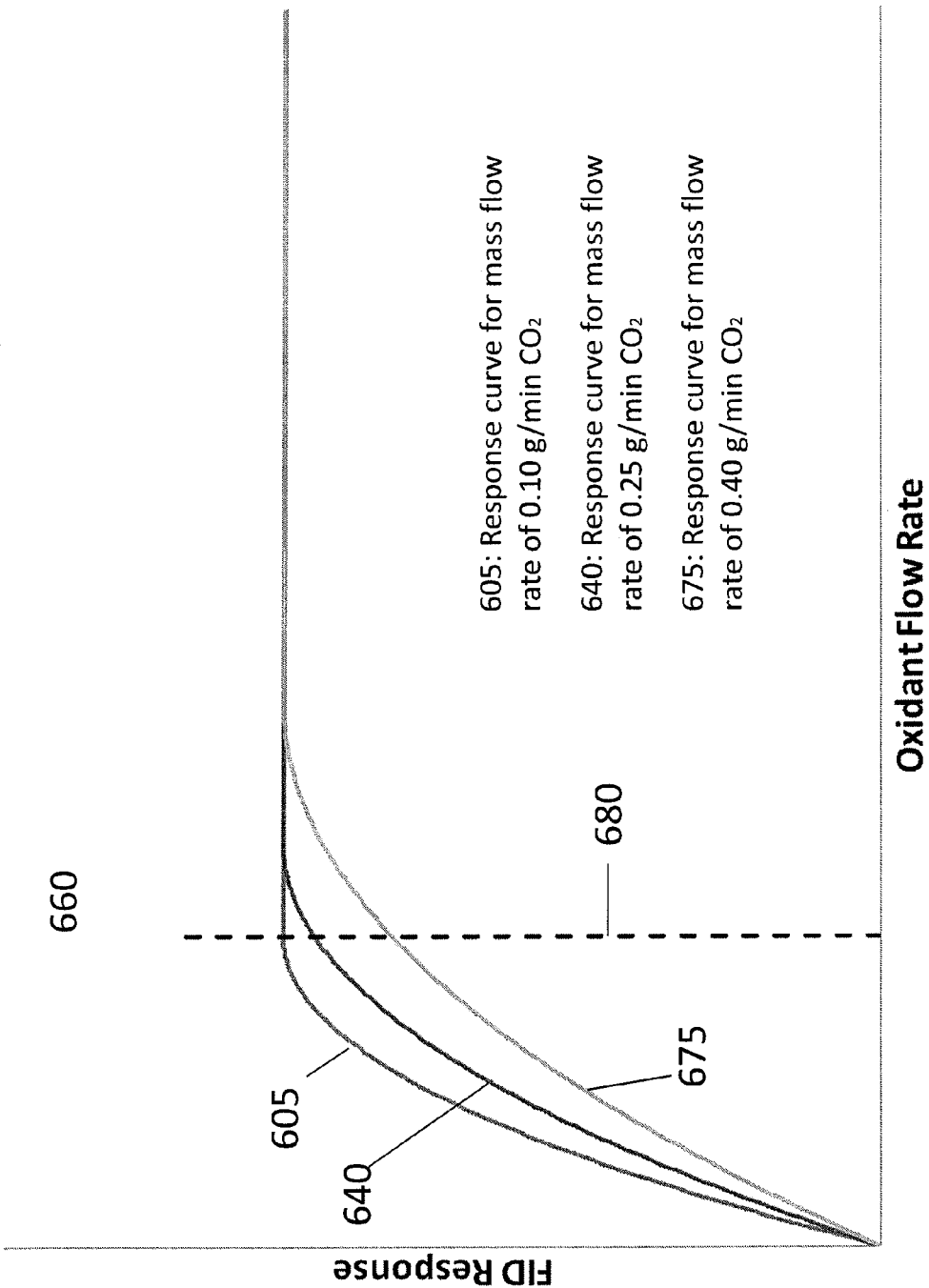
FIG. 6C shows a graphical representation of the response of a flame-based detector optimized for an oxidant mass flow rate for a first mass flow rate of mobile phase and the effect of a second and third mass flow rate of mobile phase.

FIG. 6C shows a graph (660) illustrating the theoretical response of a flame-based detector as a function of oxidant (e.g., air) mass flow rate when the oxidant mass flow rate is set to accommodate a mobile phase (e.g., $CO_2$) mass flow rate of about 0.10 g/min (605), about 0.25 g/min (640), and about 0.40 g/min (675). Similar to FIG. 6B, when the flame-based detector response is optimized for a first mobile phase mass flow rate (e.g., about 0.10 g/min), the detector response when the mobile phase entering the detector is set to the second or the third mass flow rate (e.g., about 0.25 g/min or 0.40 g/min) is suboptimal (see dashed line 680). The impact on the response of the flame-based detector can become greater the more a mobile phase mass flow rate deviates from the mobile phase mass flow rate used to optimize the detector. The change in mobile phase mass flow rate from a first to a second to a third (e.g., from about 0.10 g/min to about 0.25 g/min and/or about 0.40 g/min) can occur over the course of a chromatographic separation as a result of a density gradient. Therefore a change in mass flow rate of mobile phase (e.g., carbon dioxide) without re-optimizing the detector response, can result in suboptimal performance of a flame-based detector.

Figure 7A:
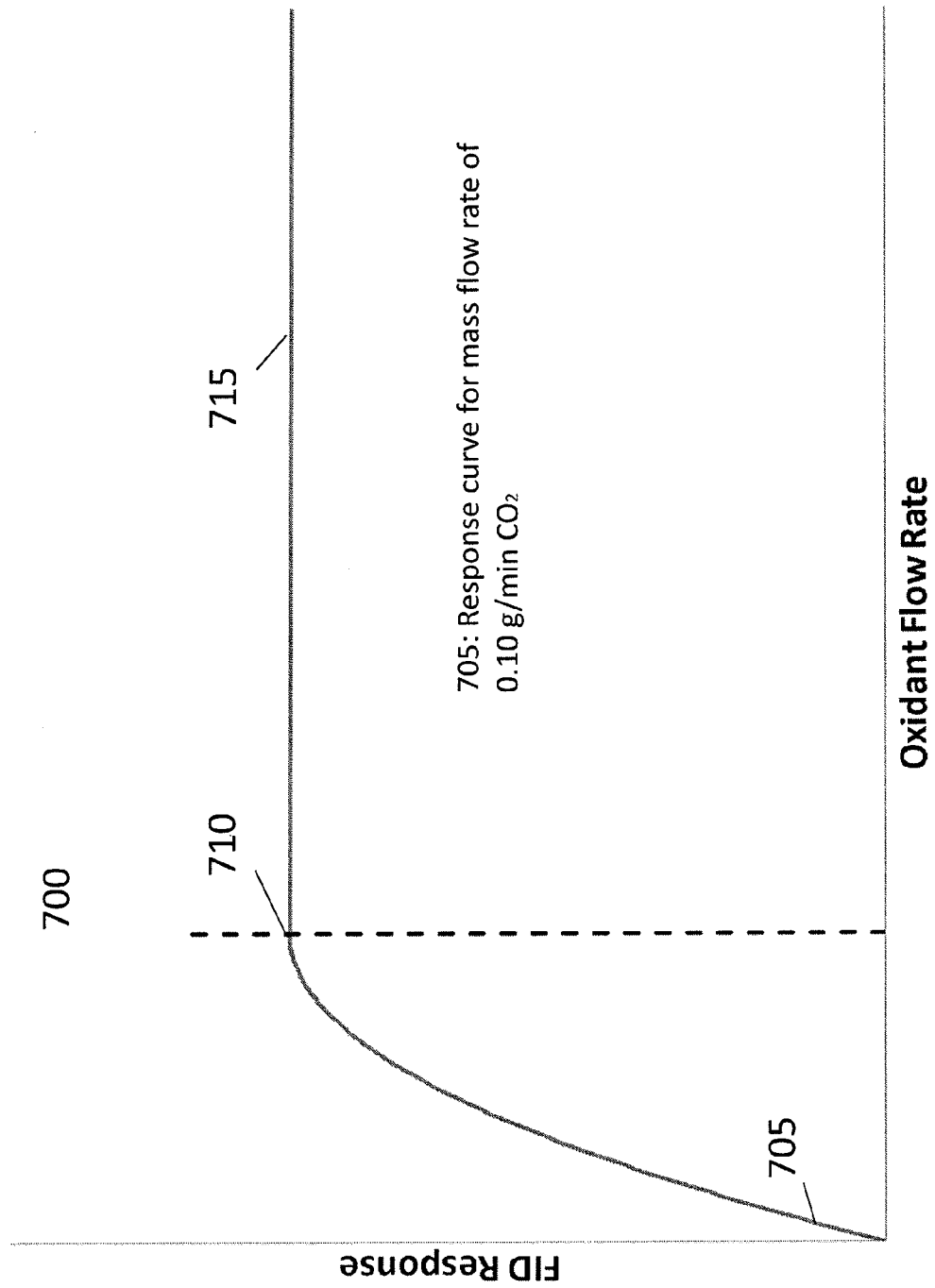
FIG. 7A shows a graphical representation of the response of a flame-based detector optimized for an oxidant mass flow rate for a first mass flow rate of mobile phase.

FIG. 7A is a graph (700) illustrating the theoretical optimized response of a flame-based detector as a function of oxidant (e.g., air) mass flow rate when the oxidant mass flow rate is set to accommodate a mobile phase (e.g., $CO_2$) mass flow rate of about 0.10 g/min. The response curve (705) shows a maximum flame-based detector response (710) at an intermediate oxidant mass flow rate. The maximum detector response plateaus at higher mass flow rates of oxidant flow (715).

Figure 7B:
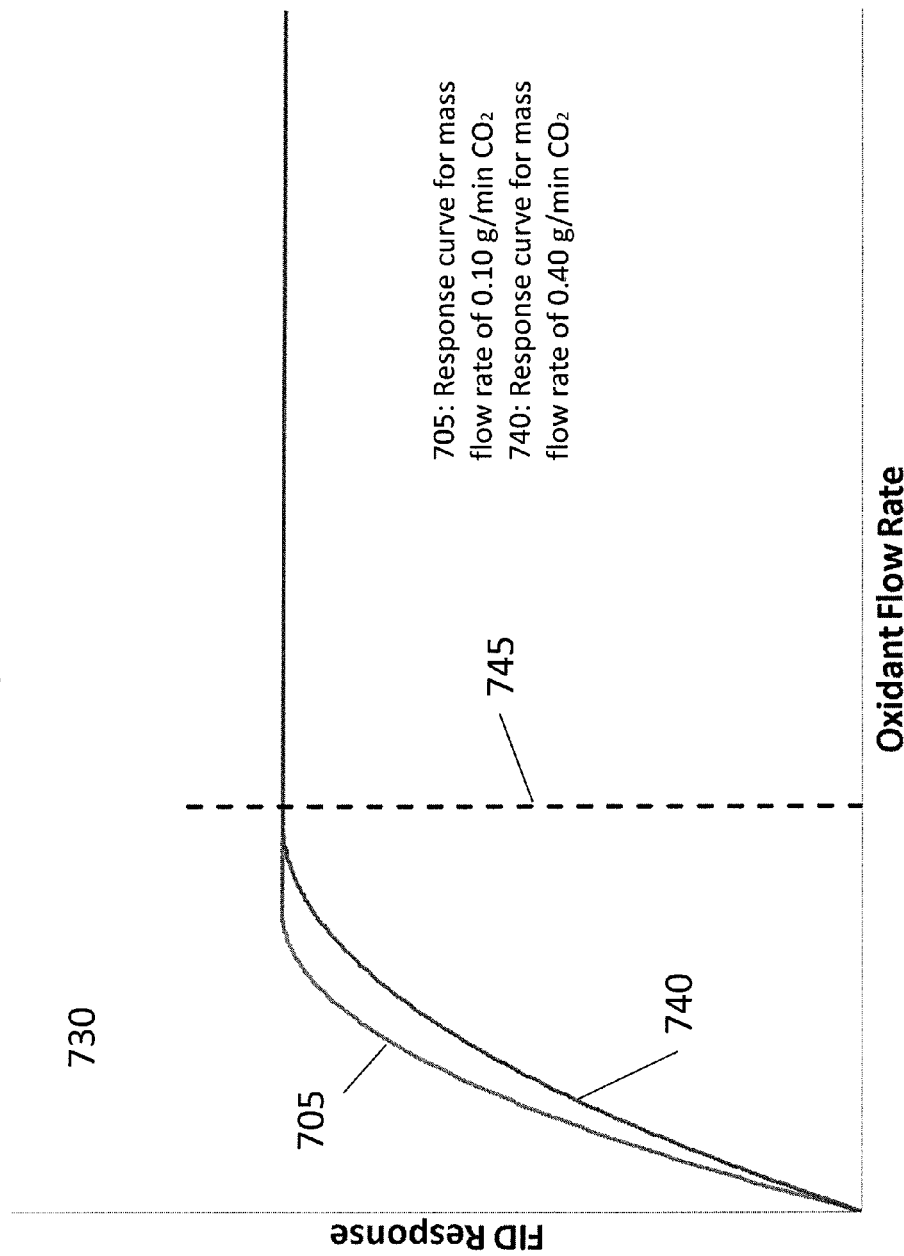
FIG. 7B shows a graphical representation of the response of a flame-based detector optimized for an oxidant mass flow rate for a second mass flow rate of mobile phase.

FIG. 7B shows a graph (730) illustrating the theoretical response of a flame-based detector as a function of oxidant (e.g., air) mass flow rate when the oxidant mass flow rate is set to accommodate a mobile phase (e.g., $CO_2$) mass flow rate of about 0.10 g/min (705) and about 0.25 g/min (740). As shown, the mass flow rate of oxidant can be increased to optimize the flame-based detector response when the mobile phase entering the detector is set to the second mass flow rate (740), for instance about 0.25 g/min (see dashed line 745). In the embodiment shown in the graph 730, setting the oxidant flow rate to accommodate the second mobile phase mass flow rate (740), for instance about 0.25 g/min also gives an optimized response for a first mobile phase mass flow rate (705), for instance about 0.10 g/min.

FIG. 7C shows a graph (760) illustrating the theoretical response of a flame-based detector as a function of oxidant (e.g., air) mass flow rate when the oxidant mass flow rate is set to accommodate a mobile phase (e.g., $CO_2$) mass flow rate of about 0.10 g/min (705), about 0.25 g/min (740), and about 0.40 g/min (775). As shown, the mass flow rate of oxidant can be increased to optimize the flame-based detector response when the mobile phase entering the detector is set to the third mass flow rate (775), for instance about 0.40 g/min (see dashed line 780). In the embodiment shown in graph 760, setting the oxidant flow rate to accommodate the third mobile phase mass flow rate (775), for instance about 0.40 g/min also gives an optimized response for a first mobile phase mass flow rate (705), for instance about 0.10 g/min and a second mobile phase mass flow rate (740), for instance about 0.25 g/min.

FIG. 8A is a graph (800) illustrating the theoretical optimized response of a flame-based detector as a function of oxidant (e.g., air) mass flow rate when the oxidant mass flow rate is set to accommodate a mobile phase (e.g., $CO_2$) mass flow rate of about 0.10 g/min. The response curve (805) reaches a maximum flame-based detector response (810) at an intermediate oxidant mass flow rate. The maximum detector response plateaus at higher mass flow rates of oxidant flow (815), and the detector response remains substantially at the maximum point at higher mobile phase mass flow rates. Accordingly, as shown in Graph 800, it is possible to set the oxidant mass flow rate to a value higher than the point at which the response begins to plateau (as shown by dashed line 820) and still achieve a maximum or substantially maximum response of the flame-based detector.

Figure 8B:
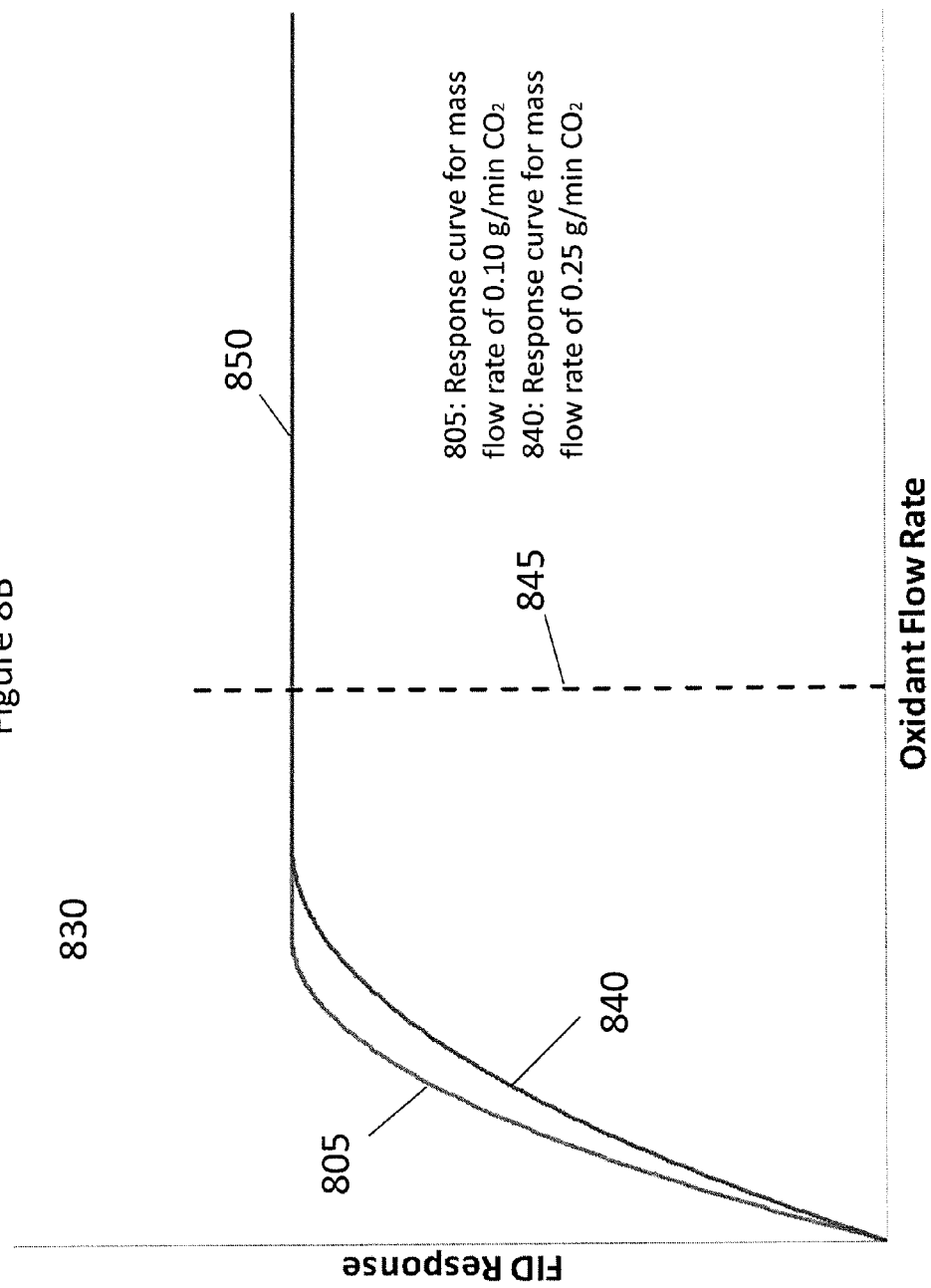
FIG. 8B shows a graphical representation of the response of a flame-based detector to an oxidant mass flow rate, wherein the oxidant mass flow rate is set to accommodate at least two different mobile phase mass flow rates.

FIG. 8B is a graph (830) illustrating the theoretical optimized response of a flame-based detector as a function of oxidant (e.g., air) mass flow rate when the oxidant mass flow rate is set to accommodate a mobile phase (e.g., $CO_2$) mass flow rate of about 0.10 g/min (805) and about 0.25 g/min (840). The response curves 805 and 840 both reach a maximum flame-based detector response at high rates of oxidant flow, and the detector response remains substantially at the maximum point at higher mobile phase mass flow rates (850). Accordingly, as shown in graph 830, it is possible to set the oxidant mass flow rate to a value higher than the point at which the response curves 805 and 840 begin to plateau (as shown by dashed line 845) and still achieve a maximum or substantially maximum response of the flame-based detector.

Figure 8C:
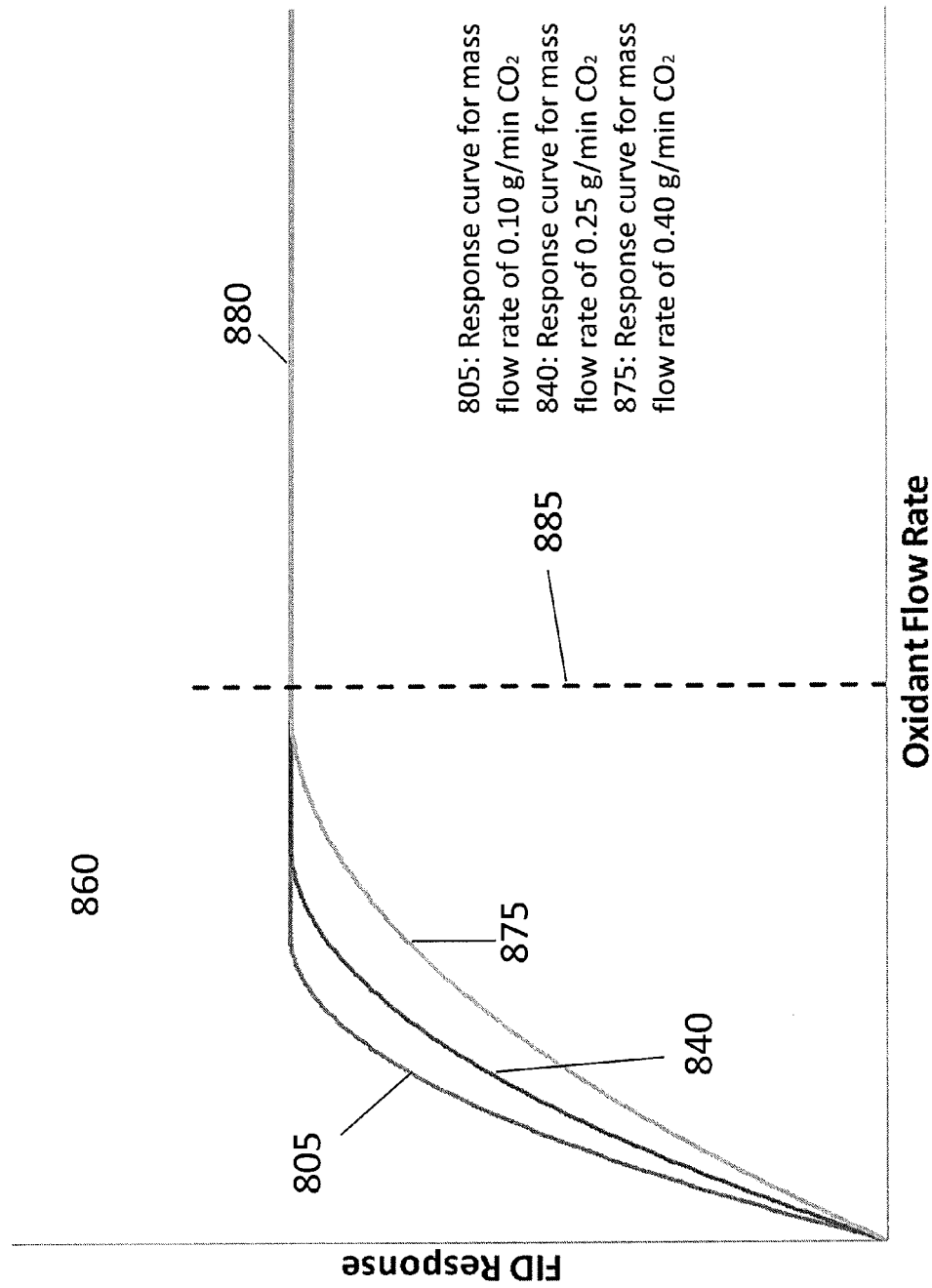
FIG. 8C shows a graphical representation of the response of a flame-based detector to an oxidant mass flow rate, wherein the oxidant mass flow rate is set to accommodate at least three different mobile phase mass flow rates.

FIG. 8C is a graph (860) illustrating the theoretical optimized response of a flame-based detector as a function of oxidant (e.g., air) mass flow rate when the oxidant mass flow rate is set to accommodate a mobile phase (e.g., $CO_2$) mass flow rate of about 0.10 g/min (865), about 0.25 g/min (870), and about 0.40 g/min (875). The response curves 805, 840 and 875 all reach a maximum flame-based detector response at intermediate rates of oxidant flow, and the detector response remains substantially at the maximum point at higher mobile phase flow rates (880). Accordingly, as shown in graph 860, it is possible to set the oxidant mass flow rate to a value higher than the point at which the response curves 805, 840 and 875 begin to plateau (as shown by dashed line 885) and still achieve a maximum or substantially maximum response of the flame-based detector.

Figure 9:
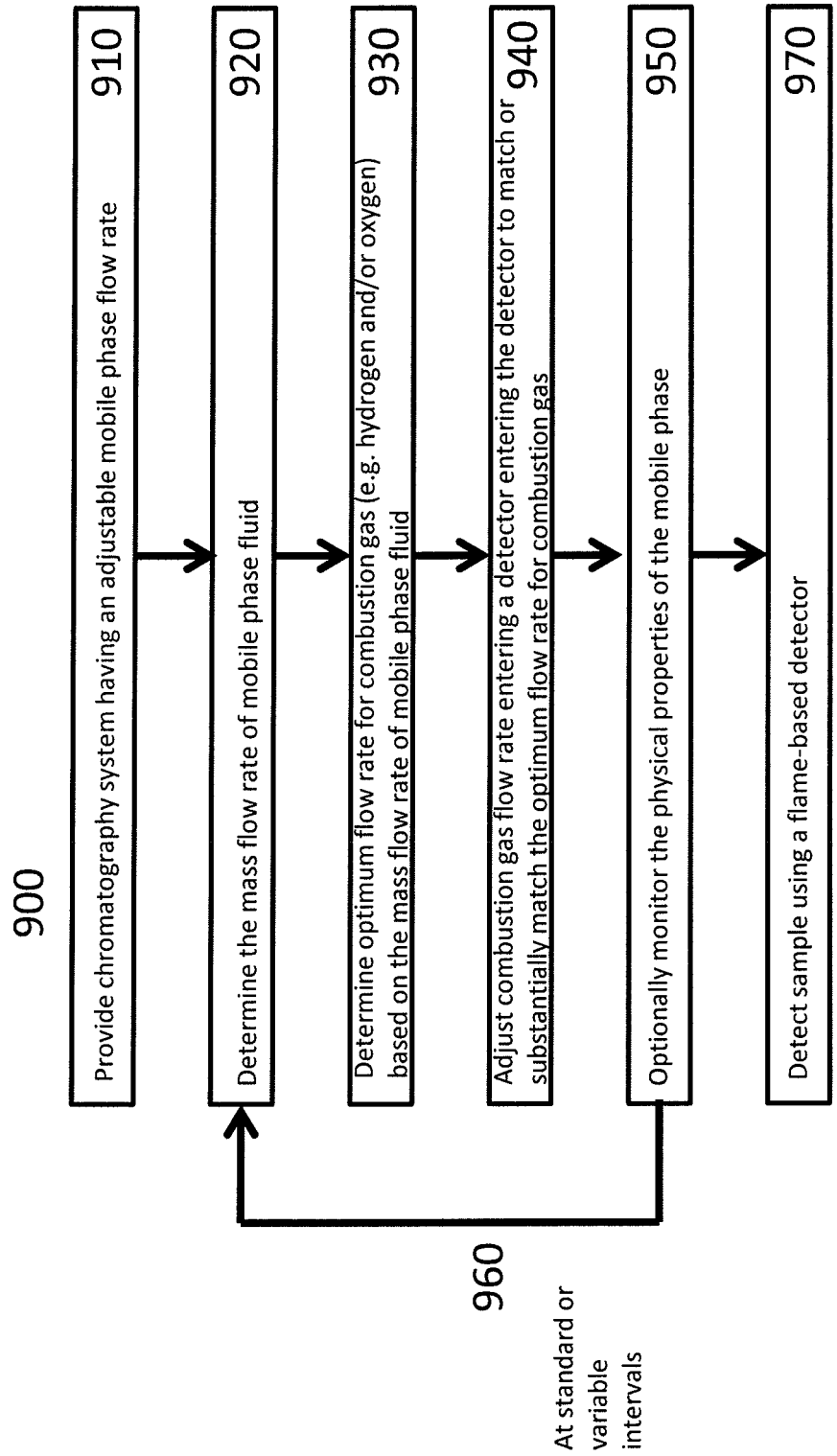
FIG. 9 shows a flow chart of one embodiment of a method for using the technology.

FIG. 9 shows a flow diagram (900) of one embodiment of the method of the current technology wherein changes to the mobile phase mass flow rate during a separation is used to adjust the FID combustion gas flow rates based on a known profile. In other embodiments, the FID-flame characteristics may be monitored to indicate FID performance as a function of mobile phase mass flow rate changes, and FID combustion gas flow rates can be adjusted accordingly. First, as indicated by step 910, a chromatography system having a variable mobile phase flow rate directed to the detector in fluid communication with a flame-based detector and upstream of the detector is provided. In the next step (920), the mass flow rate of mobile phase fluid directed to the detector is determined. The mass flow rate can be determined based on a calculation of data gathered from sensors. For instance, sensors can relay information about the volumetric flow rate of mobile phase fluid and density and/or pressure and/or temperature of mobile phase fluid at a given time point (e.g., in real time). Based on data from the sensors, a computer can calculate the mass flow rate of mobile phase directed to the detector in real time. In another embodiment, the mass flow rate of mobile phase directed to the detector can be pre-determined. For instance, a practitioner can choose to pre-set certain physical characteristics of the mobile phase such as the volumetric flow rate of mobile phase fluid and density of mobile phase fluid before beginning a separation. A practitioner can choose to pre-set a density gradient wherein the density of the mobile phase increases (or decreases) over the course of a separation. In this case, the mass flow rate of mobile phase fluid directed to the detector at a given time point during the separation can be known in advance of performing the separation.

Next, shown in step 930, an optimum flow rate for combustion gas (e.g., hydrogen and/or oxygen) based on the mass flow rate of mobile phase fluid directed to the detector is determined. The optimum flow rate of combustible fuel (e.g., hydrogen) for a given mobile phase flow rate directed to the detector can be known in advance (e.g., based on empirical observation). In some embodiments, the optimum flow rate for combustion gas can be calculated (e.g., the combustion gas flow rate can be a simple percentage of the total flow rate). After the flow rate is determined, the combustion gas flow rate entering a detector is adjusted (step 940) to match or substantially match the optimum flow rate for combustion gas based on the determination step (930). Optionally, the method can further include a step (950) of monitoring the physical properties of the mobile phase. In some embodiments, monitoring the properties of the mobile phase can include monitoring the density, volumetric flow rate, temperature, viscosity, pressure, or other physical properties of the mobile phase. As shown in item 960, the technology can include the additional, optional, step of determining the mass flow rate of mobile phase based on the data from the monitoring step (950). Thus the technology can include continuously monitoring the mass flow rate of mobile phase and adjusting the flow rate of combustion gas accordingly (960). Finally, in step (970), a sample is detected using a flame-based detector. The flame-based detector can be for example a flame photometric detector or a flame ionization detector.

The technology can include adding an amount of combustion gas (e.g., hydrogen and/or oxygen) in an amount directly proportional to the mass of mobile phase fluid entering a flame-based detector. For instance, the technology can include maintaining the combustion gas flow rate at a certain percentage of to total mass flow rate. The amount of combustible fuel (e.g., hydrogen) can be maintained independently of the amount of oxidant (e.g., air) entering the detector at a given time point. Alternatively, the ratio of combustible fuel to oxidant can be maintained at a constant ratio such that adjustment of one automatically brings about a corresponding adjustment in the other. For instance, the ratio of the combustible fuel (e.g., hydrogen) and oxidant (e.g., air) within the combustion gas can be set at a predetermined stoichiometry of 2:1 oxidant to combustible fuel (e.g., 2:1 oxygen:hydrogen or 10:1 air:hydrogen by number of moles). The technology can also include adding an amount of combustion gas according to a specific formula based on data from sensors within the chromatography system (e.g., data about the mass flow rate and density of the mobile phase). The formula can be designed to optimize the response of a flame-based detector (e.g., the formula can be designed to optimize the signal to noise ratio of the detector response).

In some embodiments, the ratio of decompressed mobile phase flow to combustible fuel to oxidant can be based on previous experience. For instance, it can be known empirically for a given detector that the response is optimized using ratio of decompressed mobile phase flow:combustible fuel:oxidant is 40:55:600 (by volume). Other exemplary ratios of decompressed mobile phase:combustible fuel:oxidant are 100:90:900, or 750:220:620, or 1.5:22:350, or 0.5:30:300, or 2:45:450.

In some embodiments, the ratio of decompressed mobile phase to combustible fuel that gives an optimized detector response is determined by experimentation for a specific detector. Methods of determining an optimal ratio of decompressed mobile phase to combustible fuel are known to one of ordinary skill in the art and are illustrated below in Example 5.

In some embodiments, the combustion gas can include hydrogen gas as the combustible fuel. In some embodiments, the combustion gas can include hydrogen gas and an oxidant. In one or more embodiments, the oxidant is air.

In one or more embodiments, the flow stream entering the detector can include the combustion gas and a non-combustion portion of the flow stream. The non-combustion portion of the flow stream can include the mobile phase from the chromatography system. The non-combustion portion of the flow stream can also include a substantially inert makeup gas. The combustion portion of the flow stream can include the combustion gas. In some embodiments, the mobile phase, the makeup gas, and the fuel are pre-mixed and enter the flame together. In most cases, the oxidant is not pre-mixed with any other flow stream and supports the flame from the outside (i.e., a diffusion flame).

The present technology can be used in chromatography systems that employ a variety of mobile phase fluids. For instance, the technology can be used in chromatography systems that use carbon dioxide, argon, xenon, fluorocarbons, ammonia, nitrous oxide, nitrogen, helium, sulfur hexafluoride ($SF_6$), or chlorofluorocarbons (CFCs) as a mobile phase. The mobile phase can be compressed in the course of a separation. The mobile phase can also be heated or cooled, or it can be both compressed and either heated or cooled. In some embodiments, the mobile phase contains at least about 50% carbon dioxide, about 55% carbon dioxide, about 60% carbon dioxide, about 65% carbon dioxide, about 70% carbon dioxide, about 75% carbon dioxide, about 80% carbon dioxide, about 85% carbon dioxide, about 90% carbon dioxide, about 95% carbon dioxide, about 98% carbon dioxide, about 99% carbon dioxide, or 100% carbon dioxide.

In some embodiments, a processor or computer receives input from sensors (e.g., system pressure transducer or mobile phase flow rate sensor) adapted to sense the flow characteristics of the mobile phase (e.g., carbon dioxide). For instance, the sensors can determine information about the pressure of the mobile phase within the chromatography system (e.g., within the chromatography column). The sensors can also determine information about the mobile phase mass flow rate. The sensors can also determine information such as the temperature and other physical properties of the mobile phase. The sensors can operate in real time and relay information to a computer or processor in real time. For instance, the sensors can relay information to a computer or processor instantly and continuously, or at certain time points (e.g., every second, or every 10 seconds). Based on data derived from the sensors, the processor or computer can calculate the total mass flow rate of mobile phase fluid entering the detector. In preferred embodiments, the optimum mass flow rate of combustion gas (e.g., hydrogen and oxygen) is known for all or substantially all mass flow rates of mobile phase fluid (e.g., carbon dioxide) to maintain a stable flame and provide optimum sensitivity for the detector. Accordingly, in preferred embodiments, the processor or computer can calculate the mass flow rate of mobile phase fluid entering a flame-based detector in substantially real time and accordingly adjust the mass flow rate of combustion gases entering the flame-based detector in substantially real time. In preferred embodiments, the mass flow rate of combustion gases entering the flame-based detector is adjusted to, and maintained at, the optimal mass flow rate for combustion gas for the given mobile phase flow rate.

In some embodiments, a density programmed gradient profile is set up in advance of a chromatographic separation. Therefore, the mass flow rate of mobile phase fluid (e.g., carbon dioxide) entering a detector at a given time point is known in advance of performing the separation. Thus, the optimum mass flow rate of combustion gases (e.g., hydrogen and oxygen) can also be calculated in advance of performing a chromatographic separation, and the processor or computer can direct the optimum mass flow rate of combustion gases to the flame-based detector based on the calculated mass flow rate of mobile phase flow (e.g., carbon dioxide) to the detector. In some preferred embodiments, sensors (e.g., system pressure transducers or mobile phase flow rate sensors) can monitor characteristics of the mobile phase (e.g., mass flow rate, temperature, density or volumetric flow rate of the mobile phase) to provide supplemental information to the computer or processor to ensure that the pre-calculated mass flow rate of mobile phase fluid matches the actual real-time mass flow rate of mobile phase fluid. The processor or computer can then make adjustments to the mass flow rate of combustion gas entering the detector, or the total volumetric flow, based on the additional data provided by the sensors of the mobile phase mass flow rate.

In some embodiments, the mass flow rate of a makeup gas (e.g., nitrogen) can be adjusted instead of, or in addition to, the mass flow rate of combustion gases (e.g., hydrogen and oxygen). For instance, the total mass flow rate of all gases can be held constant, and the individual mass flow rates of the combustion gases (e.g., hydrogen and oxygen) entering the detector can be held constant over the course of a separation. Accordingly, the mass flow rate of makeup gas can be held in inverse proportion to the mass flow rate of mobile phase fluid. The total mass flow rate of makeup gas and mobile phase fluid can be constant over the course of a separation. For instance, the total mass flow rate of mobile phase fluid entering a flame-based detector can be low at the beginning of a separation. Accordingly, the total mass flow rate of makeup gas entering the detector at the beginning of the separation can be high. As the total mass flow rate of the mobile phase increases (or decreases) over the course of the separation (e.g., as a result of a density program), the total mass flow rate of makeup gas can decrease (or increase), so that the combined mass flow rate of mobile phase fluid plus makeup gas is constant.

All, or substantially all, of the mobile phase flow stream can be directed from a chromatography separation column to a flame-based detector. Alternatively, a portion of the mobile phase flow stream can be directed from a chromatography separation column to a flame-based detector. The mobile phase can be introduced via a split from the main mobile phase flow stream or directly introduced from the chromatography column outlet. A back pressure regulator, a fixed restrictor, or a thermally modulated variable restrictor can be used to maintain system pressure upstream of the detector.

In addition to adjustments to mobile phase or gas flows, physical features of the detector may be adjusted to minimize the effect of changing mobile phase mass flow rates during the separation on the FID response. For example, the distance between a burner of a flame-based detector and a collector electrode of the flame-based detector can be adjusted according to the size of the flame. For instance, the distance can be adjusted in relation to the size of the flame. For example, a low mass flow rate of combustion gas (e.g., hydrogen) to a flame-based detector can result in a small flame whereas a high mass flow rate of combustion gas can result in a larger flame. A small flame can require less distance between the burner of a flame-based detector and the collector electrode for optimum performance. Alternatively, a larger flame can require a larger distance between the burner and collector electrode of a flame-based detector for optimal performance. Accordingly, the distance between the burner and a collector electrode of a flame-based detector can be adjusted in relation to the size of the flame. In another example, the FID burner size may be adjusted. A larger burner orifice produces a lower and broader flame. A smaller burner orifice produces a taller and narrower flame. The burner size may be changed between separation or during a separation in response to monitoring the FID response.

The present technology can be adapted for use in a number of chromatographic systems. For instance, the present technology can be adapted for use in gas chromatography (GC), dense GC or solvating GC separation schemes. The present technology can also be adapted for supercritical fluid chromatography. The chromatography system can operate on a number of different scales, for instance, preparative, semi-preparative, analytical, capillary, or microfluidic scale. The present technology can be adapted to work with a variety of different column types with a variety of different stationary phase media known in the art. For instance, the chromatography columns can be packed bed columns or open tubular columns. Additionally, the columns can be prepared in metallic, fused silica, or polymeric tubes or in metallic, ceramic, glass or polymeric microfluidic platforms. The present technology can be adapted for use in columns of various internal diameter. For instance, the internal diameter of the chromatography columns may range from 2.1 to about 4.6 mm internal diameter for analytical scale instruments, from about 0.1 to about 1.0 mm internal diameter for micro-scale instruments, from about 20 to about 300 um for capillary scale instruments, and about 4.6 to about 5.0 mm or larger for semi-preparative scale, pilot scale, and plant scale instruments.

Additionally, although some embodiments of the technology are directed to optimizing the flame characteristics over the course of a single separation, the technology can also be directed to optimizing the flame characteristics between different chromatographic runs. For instance, an operator can perform a separation at a mobile phase flow rate of 1 mL/min at 3000 psi. The system can be set up sense the relevant mass flow rate of mobile phase and optimize the flame automatically. The operator can then decide to perform a separation at 2 mL/min and 2000 psi. and The system can be set up to automatically determine the optimal gas flow rate for the second separation and automatically optimize the flame accordingly.

Figure 10:
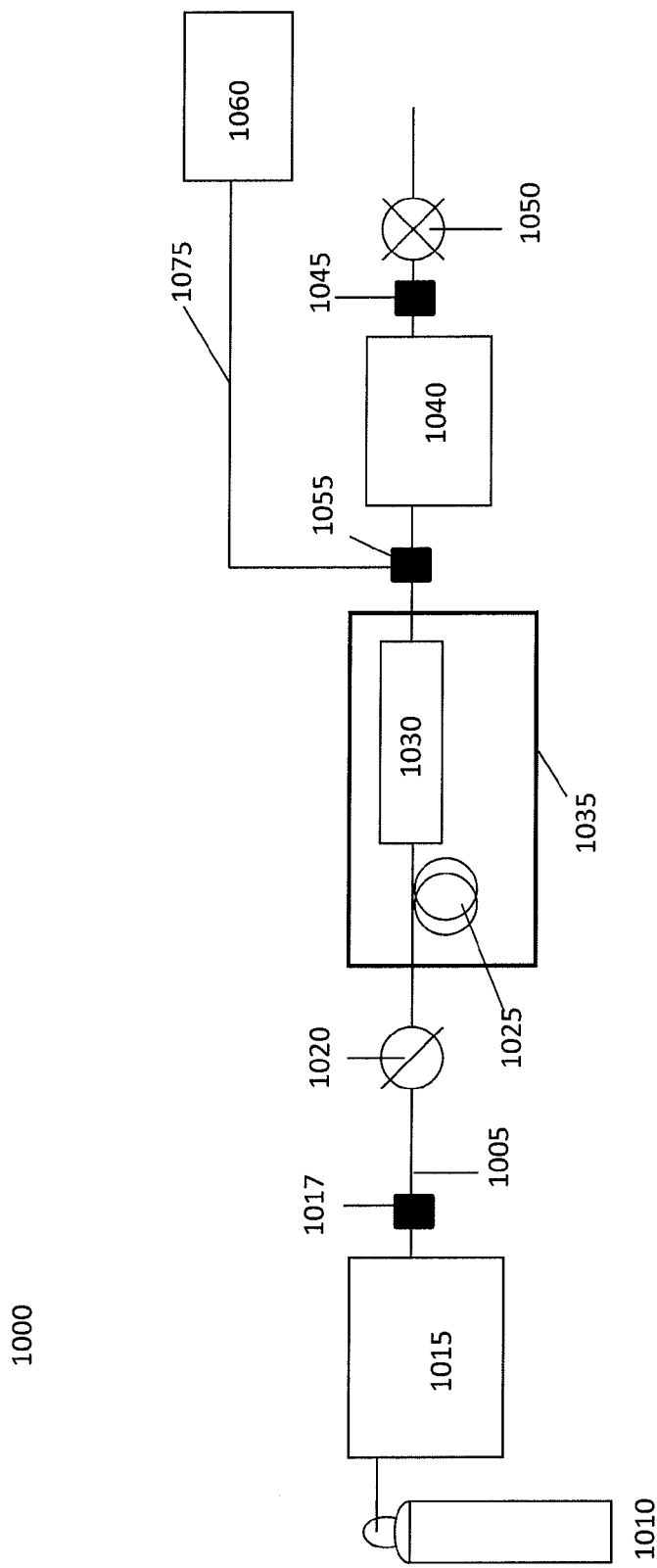
FIG. 10 shows a schematic block diagram of a chromatography apparatus that can employ the present technology.
Figure 12:
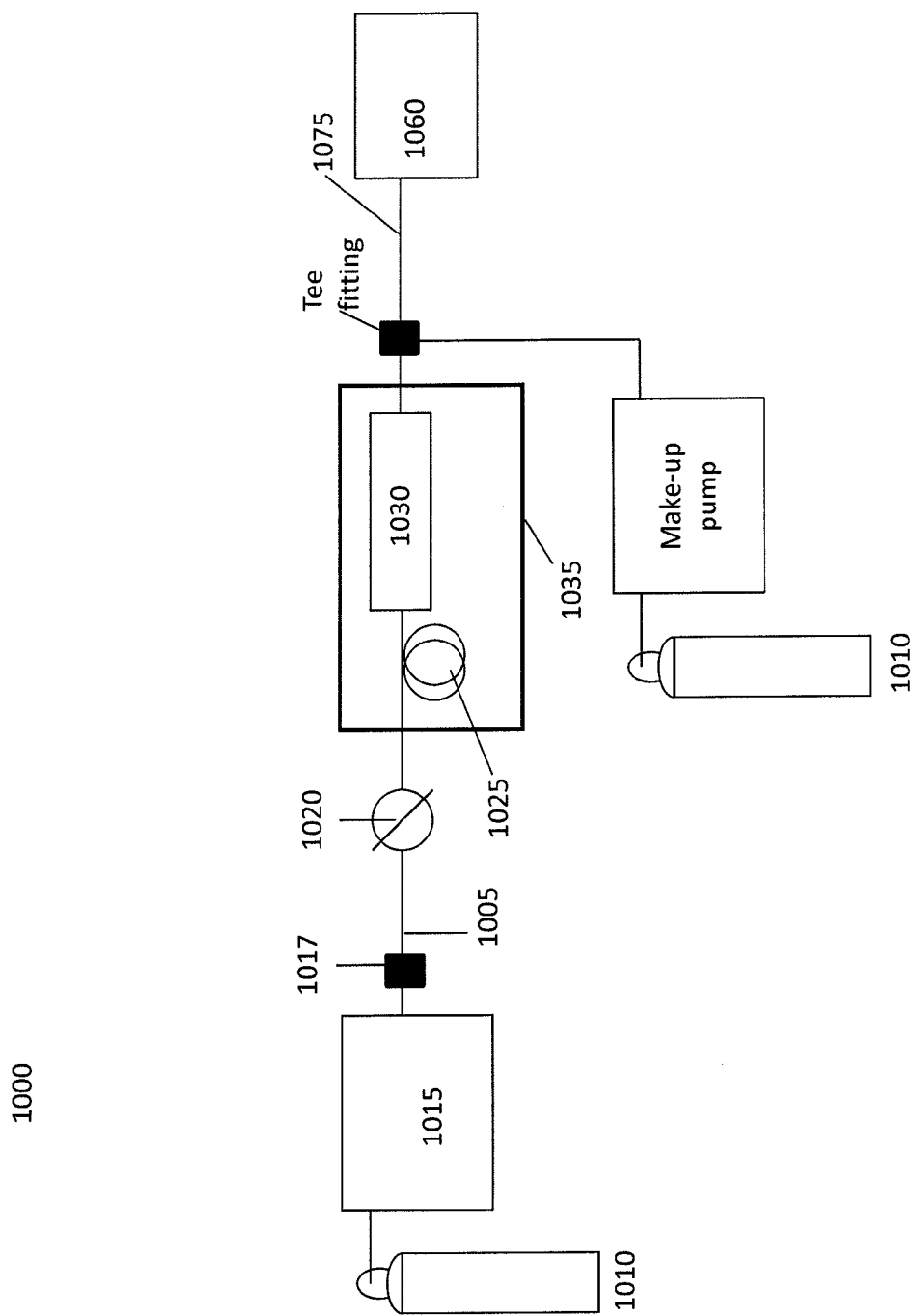
FIG. 12 shows another schematic block diagram of a chromatography apparatus that can employ the present technology.

FIG. 10 shows an exemplary block diagram of a chromatography apparatus that can employ the present technology. FIG. 10 shows one embodiment using compressed carbon dioxide as a mobile phase, although a number of compressible fluids can be used as the mobile phase, as described above. As shown in the figure, the chromatography system (1000) is interconnected and held together in fluid communication using interconnected tubing (1005). A tank of $CO_2$ (1010) is used as the source of the $CO_2$ mobile phase. The $CO_2$ is pumped through the system by a $CO_2$ pump (1015). Samples can be injected into the chromatographic system by use of a sample injector (1020). The sample can then be eluted through the chromatography system as part of the mobile phase through a preheating element (1025) and a separation column (1030), both of which can be held at a constant temperature in a column oven (1035). The mobile phase can be split (1055), with a portion of the mobile phase directed through an optional restrictor (1075) to a flame-based detector (1060). The remaining portion of the mobile phase is directed to an optional optical detector (1040) and through a back pressure regulator (1050). Optionally, the chromatography system (1000) further includes a mass flow meter (1017) located between the $CO_2$ pump and the sample injector. The chromatography system further optionally includes a pressure transducer (1045) located downstream of the optical detector (1040) and upstream of the back pressure regulator (1050). FIG. 12 shows another embodiment of a chromatography apparatus that can employ the present technology. This embodiment includes a make-up pump to supplement the mobile phase flow entering the detector.

The present technology can be adapted for use with a number of flame-based detectors. For instance, the technology can be adapted for use with flame ionization detectors (FID), flame photometric detectors (FPD), or with custom-built or free standing detectors, or with detectors operated in metallic, ceramic, glass, or polymeric microfluidic platforms.

In addition to the above description, the following non-limiting examples are provided for illustrative purposes. The specification should not be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration, and that the invention is limited only by the following claims.

EXAMPLE 1

Determining a Correlation Between Mobile Phase Mass Flow Rate to Combustion Gas Flow Rate A $CO_2$-based chromatography system with SFC capabilities (e.g., a $UPC^2$ chromatography system; commercially available from Waters Technologies Corporation, Milford, Mass., USA) was equipped with a flame ionization detector.

Compressed carbon dioxide was used as the mobile phase. The flow rate of carbon dioxide (mL/min) as a decompressed gas entering the detector was measured at four different values, shown below in Table 1. The optimal flow rate of hydrogen gas (mL/min) necessary for optimal response at each value of decompressed carbon dioxide was determined empirically by preparing a calibration curve of analyte response to hydrogen flow rate. The results are given in Table 1 below:

TABLE 1

Optimal Hydrogen Gas Flow Rate as a Function of Decompressed Carbon Dioxide Flow Rate

| Decompressed $CO_2$ flow rate at the FID (mL/min) | Required $H_2$ flow rate for optimal response (mL/min) |
|---|---|
| 14.2 | 39 |
| 37.8 | 55 |
| 100 | 90 |
| 200 | 170 |

Figure 11:
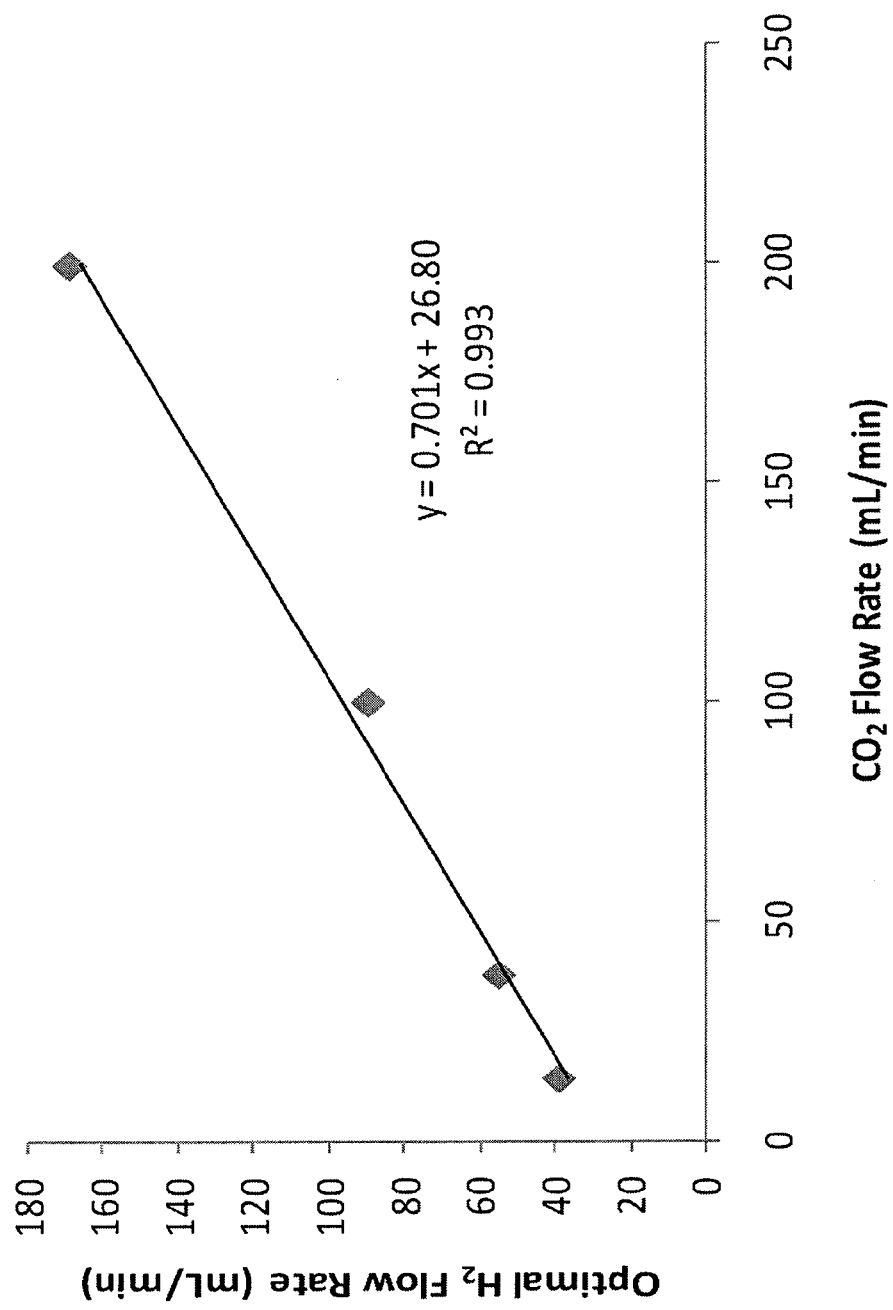
FIG. 11 shows a graph of optimized hydrogen gas flow rate for a number of different carbon dioxide flow rates for a particular flame ionization detector setup.

The results are further depicted graphically in FIG. 11. As shown in FIG. 11, the optimal hydrogen gas flow rate across the given range of decompressed carbon dioxide flow rates is defined by a linear function as y=0.701x+26.80 ($R^2$=0.993).

The above regression equation can be used to predict the appropriate flow rate of hydrogen gas ($H_2$) to maintain the detector response for a given flow rate of $CO_2$. Accordingly, a sensor can be installed downstream of the column outlet and upstream of the flame-based detector. The sensor can be in electronic communication with a computer system that controls the rate of flow of hydrogen gas to the flame-based detector. The sensor can measure the flow rate of decompressed carbon dioxide entering the detector and relay the information to the computer system. The computer system can use the measured mass flow rate of carbon dioxide entering the detector, provided from the sensor, and calculate the appropriate mass flow rate of hydrogen gas (mL/min) to the detector to maintain the flame response, based on the regression equation. Based on the calculation, the computer can then adjust the flow rate of hydrogen to the calculated value to give optimum flame response. This process can be repeated iteratively throughout the course of the chromatographic separation.

EXAMPLE 2

Adjustment of Combustion Gas Flow Rate Based on Measured Mobile Phase Mass Flow Rate A chromatographic system having an adjustable flow rate of a carbon dioxide ($CO_2$) mobile phase is provided. The chromatographic system is in fluid communication with a flame ionization detector, which is equipped with a split-flow interface (about 25:1 initial split ratio). The chromatographic system is situated upstream of the detector.

Pressure, temperature and flow rate data related to the carbon dioxide mobile phase are collected via sensors attached to the chromatographic system and relayed in real time to a microcontroller in electronic communication with the sensors. The data provided by these sensors is used to calculate the mass flow rate of $CO_2$ through the chromatographic column. Since the density of the $CO_2$ varies considerably throughout the system, the value at the pump head is used to determine mass flow. The carbon dioxide mobile phase is flowed at a rate of 0.8 mL/min with an initial back pressure of 2000 psi. The initial density of the carbon dioxide mobile phase flow stream is determined to be 0.946 g/cm$^3$, and the initial mass flow rate of carbon dioxide mobile phase to the detector is therefore determined to be 0.0291 g/min. The initial flow rate of hydrogen gas to the detector is 38 mL/min and the initial flow rate of air to the detector is 600 mL/min.

A sample is injected (sample injection volume=0.5 μL) and the back pressure is increased linearly at a rate of 100 psi/min. The mass flow rate of hydrogen gas entering the flame-based detector is adjusted in response to the increasing mass flow rate of the carbon dioxide portion of the flow stream entering the detector to maintain optimum flame characteristics. At one minute, the carbon dioxide mobile phase reaches a pressure of 2100 psi and the density of the carbon dioxide mobile phase is 0.949 g/cm$^3$. The mass flow rate of carbon dioxide mobile phase to the detector is determined to be 0.0304 g/min and the flow rate of hydrogen gas to the detector is 38.5 mL/min.

At 2 minutes the carbon dioxide mobile phase reaches a pressure of 2200 psi and the density of the carbon dioxide mobile phase is 0.955 g/cm$^3$. The mass flow rate of carbon dioxide mobile phase to the detector is determined to be 0.0318 g/min and the flow rate of hydrogen gas to the detector is 39 mL/min.

At 5 minutes the carbon dioxide mobile phase reaches a pressure of 2500 psi and the density of the carbon dioxide mobile phase is 0.969 g/cm$^3$. The mass flow rate of carbon dioxide mobile phase to the detector is determined to be 0.0369 g/min and the flow rate of hydrogen gas to the detector is 41 mL/min.

At 30 minutes, the carbon dioxide mobile phase reaches a final pressure of 5000 psi at a flow rate of 0.8 mL/min, where the pressure and flow rate are held for the remainder of the separation. The final density of the carbon dioxide mobile phase is 1.034 g/cm$^3$ and the final mass flow rate of carbon dioxide to the detector is 0.0752 g/min. The final flow rate of hydrogen gas to the detector is 56 mL/min. Throughout the separation, the mass flow rate of hydrogen gas to the detector is increased at a constant rate, or based on a pre-determined correlation, in real time by the microcontroller in proportion to the increased pressurization of the carbon dioxide mobile phase. The mass flow rate of air is maintained at a constant value of 600 mL/min throughout the separation.

EXAMPLE 3

Adjustment of Combustion Gas Flow Rate Based on Pre-Determined Mobile Phase Mass Flow Rate A chromatographic system having an adjustable flow rate of a carbon dioxide mobile phase is provided. The chromatographic system is in fluid communication with a flame ionization detector, which is equipped with a split-flow interface (about 25:1 split ratio). The chromatographic system is situated upstream of the detector.

A density gradient for the $CO_2$ mobile phase is pre-determined before beginning the chromatographic separation. The density gradient is selected based on prior separation results or theoretical considerations. The desired pressure, temperature and flow rate data related to the carbon dioxide mobile phase at every time point in the separation are input into a computer, which is converted to a theoretical mass flow rate of carbon dioxide by the computer.

During the course of the separation, data related to pressure, temperature and flow rate are also collected via sensors attached to the chromatography system and relayed in real time to the computer in electronic communication with the sensors. This ensures that the actual mass flow rate of $CO_2$ agrees with the theoretical numbers determined in advance.

The computer begins and monitors the separation upon instruction from an operator and controls the values for pressure, temperature and flow rate of mobile phase automatically. The carbon dioxide mobile phase is flowed at a rate of 0.8 mL/min with an initial back pressure of 2000 psi. The initial density of the carbon dioxide mobile phase flow stream is determined to be 0.946 g/cm$^3$, and the initial mass flow rate of carbon dioxide mobile phase to the detector is therefore determined to be 0.0291 g/min. The initial flow rate of hydrogen gas to the detector is 38 mL/min and the initial flow rate of air to the detector is 600 mL/min.

A sample is injected (sample injection volume=0.5 μL) and the computer automatically increases the back pressure linearly at a rate of 100 psi/min. The computer automatically adjusts the mass flow rate of hydrogen gas entering the flame-based detector in response to the increasing mass flow rate of the carbon dioxide portion of the flow stream entering the detector to maintain the flame characteristics. At one minute, the carbon dioxide mobile phase reaches a pressure of 2100 psi and the density of the carbon dioxide mobile phase is 0.949 g/cm$^3$. The mass flow rate of carbon dioxide mobile phase to the detector is 0.0304 g/min and the flow rate of hydrogen gas to the detector is 38.5 mL/min.

At 2 minutes the carbon dioxide mobile phase reaches a pressure of 2200 psi and the density of the carbon dioxide mobile phase is 0.955 g/cm$^3$. The mass flow rate of carbon dioxide mobile phase to the detector is 0.0318 g/min and the flow rate of hydrogen gas to the detector is 39 mL/min.

At 5 minutes the carbon dioxide mobile phase reaches a pressure of 2500 psi and the density of the carbon dioxide mobile phase is 0.969 g/cm$^3$. The mass flow rate of carbon dioxide mobile phase to the detector is 0.0369 g/min and the flow rate of hydrogen gas to the detector is 41 mL/min.

At 30 minutes, the carbon dioxide mobile phase reaches a final pressure of 5000 psi at a flow rate of 0.8 mL/min, where the pressure and flow rate are held for the remainder of the separation. The final density of the carbon dioxide mobile phase is 1.034 g/cm$^3$ and the final mass flow rate of carbon dioxide to the detector is 0.0752 g/min. The final flow rate of hydrogen gas to the detector is 56 mL/min.

Throughout the separation, the mass flow rate of hydrogen gas to the detector automatically increases at a constant rate, or based on a pre-determined correlation, in real time by the microcontroller in proportion to the calculated increased mass flow rate of the carbon dioxide mobile phase. The sensors connected to the chromatographic system monitor the pressure, temperature, and flow rate data in real time. In the event that the sensors sense values for pressure, temperature or flow rate that are outside of the pre-determined range (e.g. range ±5%), the microcontroller automatically adjusts the mass flow rate of mobile phase and hydrogen gas accordingly. The mass flow rate of air is maintained at a constant value of 600 mL/min throughout the separation.

EXAMPLE 4

Adjustment of Make-Up Gas Flow Rate Based on Per-Determined Combustion Gas Flow Rates A chromatographic system having an adjustable flow rate of a carbon dioxide mobile phase is provided. The chromatographic system is in fluid communication with a flame ionization detector, which is equipped with a split-flow interface (about 25:1 split ratio). The chromatographic system is situated upstream of the detector.

A combustion gas comprising a pre-determined ratio of hydrogen gas to oxygen is flowed to the flame-based detector. The ratio of hydrogen to oxygen in the combustion gas is optimized to ensure that the fuel and analyte is burned completely and efficiently. The combustion gas makes up a portion of the flow stream entering the detector. The combustion gas entering the detector is flowed at a rate selected to maintain the flame characteristics at the maximum expected mass flow rate of mobile phase flow. The flow rate of combustion gas does not change over the course of the separation and remains at 56 mL/min hydrogen and 600 mL air.

A stream of chemically inert nitrogen gas is flowed to the detector. The nitrogen gas acts as a surrogate for inert mobile phase carbon dioxide during points in the separation when substantially less than the maximum mass flow rate of carbon dioxide is flowing. The amount of nitrogen gas entering the detector decreases as the amount of mobile phase entering the detector increases, such that the total amount of gas (combustion gas, nitrogen gas and mobile phase) entering the detector is constant throughout the course of the separation.

Pressure, temperature and flow rate data related to the carbon dioxide mobile phase is collected via sensors attached to the chromatographic system and relayed in real time to a microcontroller in electronic communication with the sensors. The carbon dioxide mobile phase is flowed at a rate of 0.8 mL/min with an initial back pressure of 2000 psi. The initial density of the carbon dioxide mobile phase flow stream is determined to be 0.946 g/cm$^3$, and the initial mass flow rate of carbon dioxide mobile phase to the detector is therefore determined to be 0.0291 g/min. The initial flow rate of nitrogen gas to the detector is 25.0 mL/min.

A sample is injected (sample injection volume=0.5 μL) and the back pressure is increased linearly at a rate of 100 psi/min. The mass flow rate of nitrogen gas entering the flame-based detector is adjusted in response to the increasing mass flow rate of the carbon dioxide portion of the flow stream entering the detector to maintain the flame characteristics. At one minute, the carbon dioxide mobile phase reaches a pressure of 2100 psi and the density of the carbon dioxide mobile phase is 0.949 g/cm$^3$. The mass flow rate of carbon dioxide mobile phase to the detector is determined to be 0.0304 g/min and the flow rate of nitrogen gas to the detector is 24.3 mL/min.

At 2 minutes the carbon dioxide mobile phase reaches a pressure of 2200 psi and the density of the carbon dioxide mobile phase is 0.955 g/cm$^3$. The mass flow rate of carbon dioxide mobile phase to the detector is determined to be 0.0318 g/min and the flow rate of nitrogen gas to the detector is 23.5 mL/min.

At 5 minutes the carbon dioxide mobile phase reaches a pressure of 2500 psi and the density of the carbon dioxide mobile phase is 0.969 g/cm$^3$. The mass flow rate of carbon dioxide mobile phase to the detector is determined to be 0.0369 g/min and the flow rate of nitrogen gas to the detector is 20.8 mL/min.

At 30 minutes, the carbon dioxide mobile phase reaches a final pressure of 5000 psi at a flow rate of 0.8 mL/min, where the pressure and flow rate are held for the remainder of the separation. The final density of the carbon dioxide mobile phase is 1.034 g/cm$^3$ and the final mass flow rate of carbon dioxide to the detector is 0.0752 g/min. The final flow rate of nitrogen gas to the detector is 0 mL/min. Throughout the separation, the mass flow rate of nitrogen gas to the detector is decreased at a constant rate, or based on a pre-determined correlation, in real time by the microcontroller in proportion to the increased pressurization of the carbon dioxide mobile phase.

What is claimed is:

1. A method for maintaining one or more flame characteristics in a flame-based detector, the method comprising:
providing a chromatographic system having a mobile phase flow stream in fluid communication with the flame-based detector and upstream of the detector, wherein the mobile phase flow stream entering the flame-based detector has an adjustable mass flow rate;
determining a mass flow rate of a non-combustion portion of the mobile phase flow stream entering the flame-based detector; and
adjusting a mass flow rate of a combustion gas entering the flame-based detector in response to the mass flow rate of the non-combustion portion of the flow stream entering the detector to maintain the one or more flame characteristics, wherein the combustion gas is adjusted with respect to the determined mass flow rate of the non-combustion portion of the flow stream.

2. The method of claim 1, wherein the mobile phase flow stream comprises a compressible fluid suitable for use in chromatography.

3. The method of claim 2, wherein the non-combustion portion of the flow stream comprises carbon dioxide.

4. The method of claim 2, wherein the non-combustion portion of the flow stream comprises argon.

5. The method of claim 2, wherein the non-combustion portion of the flow stream comprises a CFC.

6. The method of claim 1, wherein the combustion gas comprises hydrogen, air or oxygen.

7. The method of claim 1, wherein an actual mass flow rate of the non-combustion portion of the flow stream entering the flame-based detector at a given time point is determined based on the density and volumetric flow rate of the non-combustion portion of the flow stream at that time point, and wherein the density and volumetric flow rate of the non-combustion portion of the flow stream are monitored substantially continuously by sensors coupled to a computer system.

8. The method of claim 7, wherein the computer system automatically adjusts the mass flow rate of the combustion gas entering the flame-based detector at a given time point in response to the actual mass flow rate of the non-combustion portion of the flow stream entering the detector at a given time point.

9. The method of claim 1, wherein an actual mass flow rate of the non-combustion portion of the flow stream entering the flame-based detector at a given time point is determined based on the pressure of the non-combustible portion at a split-flow interface or the mobile phase pressure at a back pressure regulator at that time point, and wherein the pressure is monitored substantially continuously by sensors coupled to a computer system.

10. The method of claim 9, wherein the computer system automatically adjusts the mass flow rate of the combustion gas entering the flame-based detector at a given time point in response to the actual mass flow rate of the non-combustion portion of the flow stream entering the detector at a given time point.

11. The method of claim 1, wherein the chromatography system is a supercritical fluid chromatographic or a gas chromatographic system.

12. The method of claim 1, wherein the mass flow rate of the combustion gas entering the flame-based detector at a given time point is pre-determined by a computer according to a pre-determined density program defining the density and volumetric flow rate of the non-combustion portion of the flow stream entering the flame-based detector at that time point.

13. The method of claim 1, further comprising adjusting the distance between a burner of the flame-based detector and a collector electrode of the flame-based detector in relation to the size of the flame.

14. The method of claim 1, further comprising adjusting the size of the burner orifice of the flame-based detector.

15. The method of claim 1, wherein a portion of the non-combustion portion of the flow stream is directed to the flame-based detector by use of a fixed restrictor to separate the flow stream.

* * * * *